United States Patent
Nebrigac

(10) Patent No.: US 11,458,274 B2
(45) Date of Patent: Oct. 4, 2022

(54) METHOD AND SYSTEMS FOR THE DELIVERY OF OXYGEN ENRICHED GAS

(71) Applicant: Inova Labs, Inc., San Diego, CA (US)

(72) Inventor: Dragan Nebrigac, Austin, TX (US)

(73) Assignee: Inova Labs, Inc., San Diego, CA (US)

(*) Notice: Subject to any disclaimer, the term of this patent is extended or adjusted under 35 U.S.C. 154(b) by 554 days.

(21) Appl. No.: 16/098,703

(22) PCT Filed: May 3, 2017

(86) PCT No.: PCT/US2017/030748
§ 371 (c)(1),
(2) Date: Nov. 2, 2018

(87) PCT Pub. No.: WO2017/192660
PCT Pub. Date: Nov. 9, 2017

(65) Prior Publication Data
US 2019/0134340 A1 May 9, 2019

Related U.S. Application Data

(60) Provisional application No. 62/330,970, filed on May 3, 2016.

(51) Int. Cl.
*A61M 16/10* (2006.01)
*A61M 16/20* (2006.01)
(Continued)

(52) U.S. Cl.
CPC ...... *A61M 16/101* (2014.02); *A61M 16/0677* (2014.02); *A61M 16/105* (2013.01);
(Continued)

(58) Field of Classification Search
CPC ............ A61M 16/101; A61M 16/0677; A61M 16/105; A61M 16/202; A61M 2205/3592;
(Continued)

(56) References Cited

U.S. PATENT DOCUMENTS 3,584,618 A 6/1971 Reinhard
3,768,468 A 10/1973 Cox
(Continued)

FOREIGN PATENT DOCUMENTS

EP 0978477 2/2000
EP 1205231 A1 5/2002
(Continued)

OTHER PUBLICATIONS

"Pressure Swing Adsorption" Douglas Morris Ruthven, Shamsuzzaman Farooq, and Kent S. Knaebel; VCH Publishers, 1994—Science.
(Continued)

*Primary Examiner* — Elliot S Ruddie
(74) *Attorney, Agent, or Firm* — Botos Churchill IP Law LLP

(57) ABSTRACT

Described herein are various embodiments of an oxygen concentrator system and method of delivering oxygen enriched gas to a user. In some embodiments, oxygen concentrator system includes one or more components that improve the efficiency of oxygen enriched gas delivery during operation of the oxygen concentrator system. In some embodiments, time measurements based on the penultimate breath taken by the user are used to alter the oxygen delivery parameters.

28 Claims, 8 Drawing Sheets

(51) Int. Cl.
  *B01D 53/047* (2006.01)
  *A61M 16/06* (2006.01)
  *A61M 16/00* (2006.01)

(52) U.S. Cl.
  CPC ......... *A61M 16/202* (2014.02); *B01D 53/047*
    (2013.01); *A61M 16/107* (2014.02); *A61M*
    *16/1055* (2013.01); *A61M 2016/0018*
    (2013.01); *A61M 2016/0024* (2013.01); *A61M*
    *2016/0027* (2013.01); *A61M 2016/0039*
    (2013.01); *A61M 2016/0042* (2013.01); *A61M*
    *2016/1025* (2013.01); *A61M 2205/18*
    (2013.01); *A61M 2205/3306* (2013.01); *A61M*
    *2205/3375* (2013.01); *A61M 2205/3569*
    (2013.01); *A61M 2205/3584* (2013.01); *A61M*
    *2205/3592* (2013.01); *A61M 2205/42*
    (2013.01); *A61M 2205/505* (2013.01); *A61M*
    *2205/587* (2013.01); *A61M 2205/7545*
    (2013.01); *A61M 2230/42* (2013.01); *B01D*
    *2253/106* (2013.01); *B01D 2253/108*
    (2013.01); *B01D 2256/14* (2013.01); *B01D*
    *2257/102* (2013.01); *B01D 2258/06* (2013.01);
    *B01D 2259/4533* (2013.01); *B01D 2259/4541*
    (2013.01)

(58) Field of Classification Search
  CPC .. A61M 2205/3306; A61M 2205/3569; A61M
    2205/505; A61M 16/1055; A61M
    2205/3375; A61M 2205/42; A61M
    16/107; A61M 2205/587; A61M
    2205/7545; A61M 2016/0024; A61M
    2205/3584; A61M 2016/0018; A61M
    2016/0027; A61M 2016/0039; A61M
    2016/0042; A61M 2016/1025; A61M
    2205/18; A61M 2230/42; B01D 53/047;
    B01D 2256/14; B01D 2253/106; B01D
    2258/06; B01D 2253/108; B01D
    2257/102; B01D 2259/4533; B01D
    2259/4541
  See application file for complete search history.

(56) References Cited

U.S. PATENT DOCUMENTS

| | | |
|---|---|---|
| 4,194,890 A | 3/1980 | McCombs et al. |
| 4,215,798 A | 8/1980 | Acharya |
| 4,302,224 A | 11/1981 | McCombs et al. |
| 4,331,455 A | 5/1982 | Sato |
| 4,342,573 A | 8/1982 | McCombs et al. |
| 4,349,357 A | 9/1982 | Russell |
| 4,491,459 A | 1/1985 | Pinkerton |
| 4,519,387 A | 5/1985 | Durkan et al. |
| 4,550,276 A | 10/1985 | Callahan et al. |
| 4,576,616 A | 3/1986 | Mottram et al. |
| 4,612,928 A | 9/1986 | Tiep et al. |
| 4,627,860 A | 12/1986 | Rowland |
| 4,630,482 A | 12/1986 | Traina |
| 4,681,099 A | 7/1987 | Sato et al. |
| 4,698,075 A | 10/1987 | Dechene |
| 4,813,979 A | 3/1989 | Miller et al. |
| 4,857,086 A | 8/1989 | Kawai |
| 4,859,217 A | 8/1989 | Chao |
| 4,892,566 A | 1/1990 | Bansal et al. |
| 4,925,464 A | 5/1990 | Rabenau et al. |
| 4,927,434 A | 5/1990 | Cordes et al. |
| 4,938,066 A | 7/1990 | Dorr |
| 4,938,212 A | 7/1990 | Snook et al. |
| 497,160 A | 11/1990 | Pawlos |
| 4,968,329 A | 11/1990 | Keefer |
| 4,971,049 A | 11/1990 | Rotariu et al. |
| 4,971,609 A | 11/1990 | Pawlos |
| 4,973,339 A | 11/1990 | Bansal |
| 4,986,269 A | 1/1991 | Hakkinen |
| 5,004,485 A | 4/1991 | Hamlin et al. |
| 5,005,571 A | 4/1991 | Dietz |
| 5,024,219 A | 6/1991 | Dietz |
| 5,048,515 A | 9/1991 | Sanso |
| 5,052,400 A | 10/1991 | Dietz |
| 5,060,506 A | 10/1991 | Douglas |
| 5,060,514 A | 10/1991 | Aylsworth |
| 5,069,221 A | 12/1991 | Smith |
| 5,069,688 A | 12/1991 | Wells |
| 5,082,473 A | 1/1992 | Keefer |
| 5,099,193 A | 3/1992 | Moseley et al. |
| 5,099,837 A | 3/1992 | Russel et al. |
| 5,108,467 A | 4/1992 | Schroter et al. |
| 5,129,924 A | 7/1992 | Schultz |
| 5,146,918 A | 9/1992 | Kallok et al. |
| 5,176,721 A | 1/1993 | Hay et al. |
| 5,223,004 A | 6/1993 | Eteve et al. |
| 5,226,933 A | 7/1993 | Knaebel |
| 5,268,021 A | 12/1993 | Hill et al. |
| 5,275,642 A | 1/1994 | Bassine |
| 5,315,990 A | 5/1994 | Mondry |
| 5,340,381 A | 8/1994 | Vorih |
| 5,351,522 A | 11/1994 | Lura |
| 5,378,345 A | 1/1995 | Taylor et al. |
| 5,469,372 A | 11/1995 | McBrearty et al. |
| 5,470,378 A | 11/1995 | Kandybin et al. |
| 5,474,595 A | 12/1995 | McCombs |
| 5,479,932 A | 1/1996 | Higgins |
| 5,503,146 A | 4/1996 | Froehlich et al. |
| 5,549,720 A | 8/1996 | Miller et al. |
| 5,575,282 A | 11/1996 | Knoch et al. |
| 5,578,115 A | 11/1996 | Cole |
| 5,593,478 A | 1/1997 | Hill et al. |
| 5,603,315 A | 2/1997 | Sasso |
| 5,672,195 A | 9/1997 | Moreau et al. |
| 5,682,877 A | 11/1997 | Mondry |
| 5,690,098 A | 11/1997 | Ottestad et al. |
| 5,697,364 A | 12/1997 | Chua et al. |
| 5,730,778 A | 3/1998 | Hill et al. |
| 5,733,359 A | 3/1998 | Doong et al. |
| 5,735,268 A | 4/1998 | Chua et al. |
| 5,746,806 A | 5/1998 | Aylsworth et al. |
| 5,764,534 A | 6/1998 | Goetting |
| 5,766,310 A | 6/1998 | Cramer |
| 5,792,665 A | 8/1998 | Morrow |
| 5,827,358 A | 10/1998 | Kulish et al. |
| 5,839,434 A | 11/1998 | Enterline |
| 5,858,062 A | 1/1999 | McCulloh et al. |
| 5,858,063 A | 1/1999 | Cao et al. |
| 5,861,694 A | 1/1999 | Niemela |
| 5,865,174 A | 2/1999 | Kloeppel |
| 5,890,490 A | 4/1999 | Aylsworth et al. |
| 5,893,944 A | 4/1999 | Dong |
| 5,906,672 A | 5/1999 | Michaels et al. |
| 5,913,307 A | 6/1999 | Taleb et al. |
| 5,917,135 A | 6/1999 | Michaels et al. |
| 5,922,107 A | 7/1999 | Labasque et al. |
| 5,928,189 A | 7/1999 | Phillips et al. |
| 5,957,133 A | 9/1999 | Hart |
| 5,961,694 A | 10/1999 | Monereau et al. |
| 5,968,236 A | 10/1999 | Bassine |
| 5,988,465 A | 11/1999 | Vitale et al. |
| 5,997,617 A | 12/1999 | Czabala et al. |
| 6,011,477 A | 1/2000 | Teodorescu et al. |
| 6,017,315 A | 1/2000 | Starr et al. |
| 6,030,435 A | 2/2000 | Monereau et al. |
| 6,065,473 A | 5/2000 | McCombs et al. |
| 6,068,680 A | 5/2000 | Kulish et al. |
| 6,099,481 A | 8/2000 | Daniels et al. |
| 6,156,101 A | 12/2000 | Naheiri |
| 6,186,142 B1 | 2/2001 | Schmidt et al. |
| 6,186,477 B1 | 2/2001 | McCombs et al. |
| 6,192,883 B1 | 2/2001 | Miller |
| 6,220,244 B1 | 4/2001 | McLaughlin |
| 6,238,458 B1 | 5/2001 | Monereau |
| 6,253,767 B1 | 7/2001 | Mantz |

(56) References Cited

U.S. PATENT DOCUMENTS

| | | |
|---|---|---|
| 6,302,107 B1 | 10/2001 | Richey et al. |
| 6,314,957 B1 | 11/2001 | Boissin et al. |
| 6,342,040 B1 | 1/2002 | Starr et al. |
| 6,346,139 B1 | 2/2002 | Czabala |
| 6,371,114 B1 | 4/2002 | Schmidt et al. |
| 6,371,117 B1 | 4/2002 | Lindqvist et al. |
| 6,382,931 B1 | 5/2002 | Czabala et al. |
| 6,394,089 B1 | 5/2002 | Cantrill et al. |
| 6,395,065 B1 | 5/2002 | Murdoch et al. |
| 6,418,782 B1 | 7/2002 | Sato et al. |
| 6,427,690 B1 | 8/2002 | McCombs et al. |
| 6,446,630 B1 | 9/2002 | Todd |
| 6,478,850 B1 | 11/2002 | Warren |
| 6,478,857 B2 | 11/2002 | Czabala |
| 6,484,721 B1 | 11/2002 | Bliss |
| 6,506,234 B1 | 1/2003 | Ackley et al. |
| 6,511,526 B2 | 1/2003 | Jagger et al. |
| 6,514,318 B2 | 2/2003 | Keefer |
| 6,520,176 B1 | 2/2003 | Dubois et al. |
| 6,527,830 B1 | 3/2003 | Neu et al. |
| 6,532,958 B1 | 3/2003 | Buan et al. |
| 6,536,431 B1 | 3/2003 | Simler |
| 6,547,851 B2 | 4/2003 | Warren |
| 6,551,384 B1 | 4/2003 | Ackley et al. |
| 6,558,451 B2 | 5/2003 | McCombs et al. |
| 6,561,187 B2 | 5/2003 | Schmidt et al. |
| 6,605,136 B1 | 8/2003 | Graham et al. |
| 6,629,525 B2 | 10/2003 | Hill et al. |
| 6,651,658 B1 | 11/2003 | Hill et al. |
| 6,655,383 B1 | 12/2003 | Lundberg |
| 6,669,758 B1 | 12/2003 | Hart et al. |
| 6,691,702 B2 | 2/2004 | Appel et al. |
| 6,694,973 B1 | 2/2004 | Dunhao et al. |
| 6,698,423 B1 | 3/2004 | Honkonen et al. |
| 6,699,307 B1 | 3/2004 | Lomax |
| 6,702,880 B2 | 3/2004 | Roberts et al. |
| 6,712,876 B2 | 3/2004 | Cao et al. |
| 6,712,877 B2 | 3/2004 | Cao et al. |
| 6,749,405 B2 | 6/2004 | Bassine |
| 6,755,895 B2 | 6/2004 | Lomax et al. |
| 6,764,534 B2 | 7/2004 | McCombs et al. |
| 6,790,260 B2 | 9/2004 | Ackley et al. |
| 6,802,889 B2 | 10/2004 | Graham et al. |
| 6,824,590 B2 | 11/2004 | Dee et al. |
| 6,827,760 B2 | 12/2004 | Kutt et al. |
| 6,837,244 B2 | 1/2005 | Yagi et al. |
| 6,866,041 B2 | 3/2005 | Hardy et al. |
| 6,866,950 B2 | 3/2005 | Connor et al. |
| 6,896,721 B1 | 5/2005 | Lynn |
| 6,908,503 B2 | 6/2005 | McCombs et al. |
| 6,918,953 B2 | 7/2005 | Lomax et al. |
| 6,929,683 B2 | 8/2005 | Lomax et al. |
| 6,935,460 B2 | 8/2005 | McCombs et al. |
| 6,938,619 B1 | 9/2005 | Hickle |
| 6,949,133 B2 | 9/2005 | McCombs et al. |
| 6,981,502 B2 | 1/2006 | McCormick et al. |
| 6,990,975 B1 | 1/2006 | Jones et al. |
| 7,000,612 B2 | 2/2006 | Jafari et al. |
| 7,007,694 B2 | 3/2006 | Aylsworth et al. |
| 7,011,091 B2 | 3/2006 | Hill et al. |
| 7,011,092 B2 | 3/2006 | McCombs et al. |
| 7,013,898 B2 | 3/2006 | Rashad et al. |
| 7,037,358 B2 | 5/2006 | Babicki |
| 7,059,323 B2 | 6/2006 | Kullik et al. |
| 7,066,985 B2 | 6/2006 | Deane et al. |
| 7,077,133 B2 | 7/2006 | Yagi et al. |
| 7,105,038 B2 | 9/2006 | Lee et al. |
| 7,114,932 B1 | 10/2006 | Bassine |
| 7,121,276 B2 | 10/2006 | Jagger et al. |
| 7,122,073 B1 | 10/2006 | Notaro et al. |
| 7,135,059 B2 | 11/2006 | Deane et al. |
| 7,156,903 B2 | 1/2007 | McCombs |
| 7,171,963 B2 | 2/2007 | Jagger et al. |
| 7,178,563 B2 | 2/2007 | Richey et al. |
| 7,179,326 B2 | 2/2007 | Nakamura et al. |
| 7,204,249 B1 | 4/2007 | Richey et al. |
| 7,213,468 B2 | 5/2007 | Fujimoto |
| 7,222,624 B2 | 5/2007 | Rashad et al. |
| 7,225,809 B1 | 6/2007 | Bowen et al. |
| 7,279,029 B2 | 10/2007 | Occhialini et al. |
| 7,306,657 B2 | 12/2007 | Yagi et al. |
| 7,329,304 B2 | 2/2008 | Bliss et al. |
| 7,329,354 B2 | 2/2008 | Mullee |
| 7,396,390 B2 | 7/2008 | Hayashi et al. |
| 7,402,193 B2 | 7/2008 | Bliss et al. |
| 7,431,032 B2 | 10/2008 | Jagger et al. |
| 7,438,745 B2 | 10/2008 | Deane et al. |
| 7,473,299 B2 | 1/2009 | Occhialini et al. |
| 7,556,038 B2 | 7/2009 | Kirby et al. |
| 7,565,907 B2 | 7/2009 | Curti et al. |
| 7,582,138 B2 | 9/2009 | Lessi et al. |
| 7,585,351 B2 | 9/2009 | Deane et al. |
| 7,604,004 B2 | 10/2009 | Jagger et al. |
| 7,604,005 B2 | 10/2009 | Jagger et al. |
| 7,686,870 B1 | 3/2010 | Deane et al. |
| 7,708,802 B1 | 5/2010 | Deane et al. |
| 7,730,887 B2 | 6/2010 | Deane et al. |
| 7,753,996 B1 | 7/2010 | Deane et al. |
| 7,757,693 B2 | 7/2010 | Toussaint |
| 7,766,010 B2 | 8/2010 | Jagger et al. |
| 7,780,768 B2 | 8/2010 | Taylor et al. |
| 7,814,906 B2 | 10/2010 | Moretti |
| 7,837,761 B2 | 11/2010 | Bliss et al. |
| 7,841,343 B2 | 11/2010 | Deane et al. |
| 7,857,894 B2 | 12/2010 | Taylor et al. |
| 7,866,315 B2 | 1/2011 | Jagger et al. |
| 7,922,789 B1 | 4/2011 | Deane et al. |
| 8,016,918 B2 | 9/2011 | Labuda et al. |
| 8,020,558 B2 | 9/2011 | Christopher et al. |
| 8,142,544 B2 | 3/2012 | Taylor et al. |
| 8,147,597 B2 | 4/2012 | Dolensky et al. |
| 2001/0004893 A1 | 6/2001 | Biondi |
| 2001/0020603 A1 | 9/2001 | Moorehead et al. |
| 2002/0038657 A1 | 4/2002 | Yagi |
| 2003/0006024 A1 | 1/2003 | Wang |
| 2003/0111081 A1 | 6/2003 | Gupta |
| 2003/0121517 A1 | 7/2003 | McFarland |
| 2003/0140924 A1 | 7/2003 | Aylsworth et al. |
| 2004/0050255 A1 | 3/2004 | Simonds |
| 2004/0074496 A1 | 4/2004 | Hayashi et al. |
| 2004/0141874 A1 | 7/2004 | Mullinax |
| 2004/0159323 A1 | 8/2004 | Schmidt et al. |
| 2004/0182394 A1 | 9/2004 | Alvey et al. |
| 2005/0027216 A1 | 2/2005 | Guillemaud |
| 2005/0066976 A1 | 3/2005 | Wondka |
| 2005/0103341 A1 | 5/2005 | Deane |
| 2005/0103343 A1 | 5/2005 | Gosweiler |
| 2005/0121033 A1 | 6/2005 | Starr et al. |
| 2005/0160905 A1 | 7/2005 | Whitley et al. |
| 2005/0192538 A1 | 9/2005 | Voege |
| 2005/0217674 A1 | 10/2005 | Burton |
| 2005/0274381 A1* | 12/2005 | Deane ............... A61M 16/026 128/204.23 |
| 2006/0084877 A1 | 4/2006 | Ujhazy et al. |
| 2006/0102181 A1 | 5/2006 | McCombs et al. |
| 2006/0112962 A1 | 6/2006 | Tebbutt et al. |
| 2006/0117957 A1 | 6/2006 | McCombs |
| 2006/0124128 A1 | 6/2006 | Deane et al. |
| 2006/0144240 A1 | 7/2006 | Lee et al. |
| 2006/0154642 A1 | 7/2006 | Scannell |
| 2006/0174871 A1 | 8/2006 | Jagger et al. |
| 2006/0174875 A1 | 8/2006 | Jagger et al. |
| 2006/0174876 A1 | 8/2006 | Jagger et al. |
| 2006/0174877 A1 | 8/2006 | Jagger et al. |
| 2006/0174880 A1 | 8/2006 | Jagger et al. |
| 2006/0174881 A1 | 8/2006 | Jagger et al. |
| 2006/0174882 A1 | 8/2006 | Jagger et al. |
| 2006/0185668 A1 | 8/2006 | Jagger et al. |
| 2006/0207594 A1 | 9/2006 | Stenzler et al. |
| 2006/0230931 A1 | 10/2006 | Bliss et al. |
| 2006/0230939 A1 | 10/2006 | Bliss et al. |
| 2006/0266357 A1 | 11/2006 | McCombs et al. |
| 2007/0039466 A1 | 2/2007 | Nawata et al. |
| 2007/0044799 A1 | 3/2007 | Hete et al. |

(56) References Cited

U.S. PATENT DOCUMENTS

| | | |
|---|---|---|
| 2007/0056583 A1 | 3/2007 | Jagger et al. |
| 2007/0056584 A1 | 3/2007 | Jagger et al. |
| 2007/0137487 A1 | 6/2007 | Whitley et al. |
| 2007/0169623 A1 | 7/2007 | Lee et al. |
| 2007/0227539 A1 | 10/2007 | Schwaibold et al. |
| 2007/0283958 A1 | 12/2007 | Naghavi |
| 2007/0293781 A1 | 12/2007 | Sims |
| 2008/0006741 A1 | 3/2008 | Lemahieu et al. |
| 2008/0053441 A1 | 3/2008 | Gottlib et al. |
| 2008/0066741 A1 | 3/2008 | Lemahieu et al. |
| 2008/0078392 A1 | 4/2008 | Pelletier et al. |
| 2008/0103404 A1 | 5/2008 | Cao |
| 2008/0110462 A1 | 5/2008 | Chekal |
| 2008/0202508 A1 | 8/2008 | McClain et al. |
| 2008/0223367 A1 | 9/2008 | Cox et al. |
| 2008/0302364 A1 | 12/2008 | Garde |
| 2009/0065007 A1 | 3/2009 | Wilkinson |
| 2009/0065526 A1 | 3/2009 | Sprinkle |
| 2009/0107500 A1 | 4/2009 | Edwards |
| 2009/0107501 A1 | 4/2009 | Krieger |
| 2009/0133699 A1 | 5/2009 | Nalagatla et al. |
| 2009/0145428 A1 | 6/2009 | Sward et al. |
| 2009/0157219 A1 | 6/2009 | Parker et al. |
| 2009/0199855 A1* | 8/2009 | Davenport ........ A61M 16/0677 128/204.23 |
| 2009/0211438 A1 | 8/2009 | Thompson et al. |
| 2009/0211448 A1 | 8/2009 | McClain |
| 2009/0241956 A1 | 10/2009 | Baker et al. |
| 2009/0306529 A1 | 12/2009 | Curti et al. |
| 2009/0308394 A1* | 12/2009 | Levi ................... A61M 16/024 128/204.23 |
| 2010/0051030 A1 | 3/2010 | Richard et al. |
| 2010/0071698 A1 | 3/2010 | Kiritake |
| 2010/0076514 A1 | 3/2010 | Cho |
| 2010/0094366 A1 | 4/2010 | McCarthy |
| 2010/0116270 A1 | 5/2010 | Edwards et al. |
| 2010/0133900 A1 | 6/2010 | King |
| 2010/0263664 A1 | 10/2010 | Radivojevic et al. |
| 2010/0282084 A1 | 11/2010 | Hansen et al. |
| 2010/0313898 A1 | 12/2010 | Richard et al. |
| 2011/0017063 A1 | 1/2011 | Van Brunt et al. |
| 2011/0017216 A1 | 1/2011 | Van et al. |
| 2011/0020143 A1 | 1/2011 | Van et al. |
| 2011/0020156 A1 | 1/2011 | Van et al. |
| 2011/0030684 A1 | 2/2011 | Wilkinson et al. |
| 2011/0030685 A1 | 2/2011 | Wilkinson et al. |
| 2011/0030686 A1 | 2/2011 | Wilkinson et al. |
| 2011/0030687 A1 | 2/2011 | Wilkinson et al. |
| 2011/0030689 A1 | 2/2011 | Wilkinson et al. |
| 2011/0046498 A1 | 2/2011 | Klap |
| 2011/0063094 A1 | 3/2011 | Meiertoberens et al. |
| 2011/0175728 A1 | 7/2011 | Baker |
| 2011/0186054 A1 | 8/2011 | Boyd |
| 2011/0232483 A1 | 9/2011 | Haberland et al. |
| 2011/0247620 A1 | 10/2011 | Armstrong et al. |
| 2011/0303223 A1 | 12/2011 | Klane |
| 2011/0315140 A1 | 12/2011 | Shuman |
| 2012/0029307 A1 | 2/2012 | Paquet |
| 2012/0055340 A1 | 3/2012 | Wilkinson et al. |
| 2012/0055474 A1 | 3/2012 | Wilkinson |
| 2012/0055475 A1 | 3/2012 | Wilkinson |
| 2012/0055477 A1 | 3/2012 | Wilkinson |
| 2012/0055478 A1 | 3/2012 | Wilkinson |
| 2012/0055480 A1 | 3/2012 | Wilkinson |
| 2012/0055483 A1 | 3/2012 | Wilkinson et al. |
| 2012/0167883 A1 | 7/2012 | Taylor et al. |
| 2012/0167886 A1 | 7/2012 | Taylor et al. |
| 2012/0167887 A1 | 7/2012 | Taylor et al. |
| 2012/0167888 A1 | 7/2012 | Taylor et al. |
| 2012/0055482 A1 | 8/2012 | Wilkinson |
| 2012/0203128 A1 | 8/2012 | Levison |
| 2012/0266883 A1* | 10/2012 | Taylor ................. B01D 53/0415 128/205.12 |
| 2013/0148020 A1 | 6/2013 | Cook |
| 2013/0172759 A1 | 7/2013 | Melker |
| 2014/0137737 A1 | 5/2014 | Wilkinson et al. |
| 2014/0137744 A1 | 5/2014 | Wilkinson et al. |
| 2014/0137859 A1* | 5/2014 | Wilkinson ........ A61M 16/0816 128/202.26 |
| 2015/0059742 A1 | 3/2015 | Wilkinson et al. |

FOREIGN PATENT DOCUMENTS

| | | |
|---|---|---|
| EP | 1568391 A1 | 8/2005 |
| EP | 1661596 A2 | 5/2006 |
| JP | H07172804 | 7/1995 |
| JP | H11514556 A | 12/1999 |
| JP | 2000354630 | 12/2000 |
| JP | 2001170177 A | 6/2001 |
| JP | 2002253675 | 9/2002 |
| JP | 2005087937 | 4/2005 |
| JP | 2005245825 | 9/2005 |
| JP | 2006095285 | 4/2006 |
| JP | 2007195820 A | 8/2007 |
| JP | 2007289660 | 11/2007 |
| JP | 2008501445 A | 1/2008 |
| JP | 2008136664 A | 6/2008 |
| JP | 2009532184 A | 9/2009 |
| JP | 2010537779 A | 12/2010 |
| JP | 4816590 | 11/2011 |
| JP | 2012183159 A | 9/2012 |
| KR | 100741307 B1 | 7/2007 |
| WO | 9922795 A1 | 5/1999 |
| WO | 9943416 A1 | 9/1999 |
| WO | 0249742 A1 | 6/2002 |
| WO | 2006108092 A1 | 10/2006 |
| WO | 2011006199 A1 | 1/2011 |
| WO | 2012033839 A2 | 3/2012 |

OTHER PUBLICATIONS

Australian Examination Report for Australian Patent Application No. 2008296606 dated Jul. 11, 2014.

Australian Examination Report for Australian Patent Application No. 2008296606 dated Mar. 27, 2013.

Dietz "international Society for Mountain Medicine: An Altitude Tutorial" Jan. 29, 2006, pp. 1-12.

EP Communication for EP Application No. 2197530 dated Feb. 5, 2014.

EP Communication for EP Application No. 2197530 dated May 24, 2012.

EP Communication for EP Application No. 2613838 dated Mar. 17, 2015.

Final Rejection Office Action dated Nov. 1, 2021 for U.S. Appl. No. 16/098,703.

Freesyle; Freestyle TM Portable Oxygen Concentrator, Patient Manual, AirSep, Revision; Jan. 27, 2006.

Hartzog, D. G. and Sircar, S., "Sensitivity of PSA Process Performance to Input Variables", Adsorption 1, 133-151 (1995).

International Preliminary Report on Patentability for PCT Application No. PCT/US2008/073884 dated Mar. 18, 2010.

Japanese Examination Report for JP Application No. 2010-524089 dated Apr. 22, 2013.

Japanese Examination Report for JP Application No. 2010-524089 dated Mar. 4, 2014.

JP Notice of Allowance dated Jan. 11, 2022 for JP Patent Application No. 2019-224548.

JP Office Action issued in corresponding JP application No. 2018-072820 dated Jan. 22, 2019.

JP Office Action dated Mar. 16, 2021 for JP Application No. 2019-224548.

Keller II. George E., et al., "A New Process for Adsorption Separation of Gas Streams", ACS Symposium Series 135, 1980, pp. 275-286.

Kopaygorodsky et al. "Scaling Analysis—A Valuable Technique in Engineering Teaching and Practice" Proceedings o the 2001 American Society for Engineering Education Annual Conference & Exposition Session 3513, 2001.

(56) References Cited

OTHER PUBLICATIONS

Kumar, R., et al., "A Versatile Process Simulator for Adsorptive Separations", Chemical Engineering Science, vol. 49, No. 18, pp. 3115-3125.
Lifestyle; Lifestyle TM Portable Oxygen Concentrator, Patient Manual, AirSep, Revision Date Dec. 2004.
Office Action for U.S. Appl. No. 12/163,549 dated Aug. 14, 2013.
Office Action for U.S. Appl. No. 12/163,549 dated Dec. 20, 2013.
Office Action for U.S. Appl. No. 12/163,549 dated May 10, 2012.
Office Action for U.S. Appl. No. 12/868,340 dated Apr. 26, 2013.
Office Action for U.S. Appl. No. 12/868,340 dated May 22, 2014.
Office Action for U.S. Appl. No. 12/868,340 dated Nov. 7, 2013.
Office Action for U.S. Appl. No. 12/868,354 dated Apr. 26, 2013.
Office Action for U.S. Appl. No. 12/868,354 dated Mar. 6, 2014.
Office Action for U.S. Appl. No. 12/868,354 dated Nov. 6, 2014.
Office Action for U.S. Appl. No. 12/868,368 dated Apr. 26, 2013.
Office Action for U.S. Appl. No. 12/868,368 dated Aug. 7, 2014.
Office Action for U.S. Appl. No. 12/868,368 dated Dec. 19, 2014.
Office Action for U.S. Appl. No. 12/868,368 dated Jan. 17, 2014.
Office Action for U.S. Appl. No. 12/868,382 dated May 22, 2013.
Office Action for U.S. Appl. No. 12/868,391 dated May 23, 2013.
Office Action for U.S. Appl. No. 12/868,340 dated Oct. 10, 2012.
Office Action for U.S. Appl. No. 12/868,354 dated Oct. 11, 2012.
Office Action for U.S. Appl. No. 12/868,368 dated Oct. 5, 2012.
Office Action for U.S. Appl. No. 12/868,382 dated Oct. 12, 2012.
Office Action for U.S. Appl. No. 12/868,391 dated Oct. 5, 2012.
Office Action for U.S. Appl. No. 12/876,848 dated May 23, 2013.
Office Action for U.S. Appl. No. 12/876,848 dated Oct. 26, 2012.
Office Action for U.S. Appl. No. 12/876,854 dated Feb. 14, 2014.
Office Action for U.S. Appl. No. 12/876,854 dated Jul. 18, 2013.
Office Action for U.S. Appl. No. 12/876,874 dated Aug. 22, 2012.
Office Action for U.S. Appl. No. 12/876,874 dated Feb. 15, 2013.
Office Action for U.S. Appl. No. 12/876,878 dated Feb. 5, 2014.
Office Action for U.S. Appl. No. 12/876,878 dated Jun. 19, 2013.
Office Action for U.S. Appl. No. 12/876,878 dated Nov. 20, 2014.
Office Action for U.S. Appl. No. 12/876,878 dated Nov. 9, 2012.
Final Office Action dated Feb. 9, 2022 for U.S. Appl. No. 17/061,973.
Notice of Allowance dated Feb. 22, 2022 for U.S. Appl. No. 15/258,510.

* cited by examiner

METHOD AND SYSTEMS FOR THE DELIVERY OF OXYGEN ENRICHED GAS Cross-Reference to Related Applications The present application is a national phase entry under 35 U.S.C. § 371 of International Application No. PCT/US2017/030748, filed May 3, 2017, published in English, which claims priority from U.S. Provisional patent application No. 62/330,970, filed May 3, 2016.

BACKGROUND OF THE INVENTION

1. Field of the Invention

The present invention relates generally to methods and system that provide oxygen enriched gas to a subject.

2. Description of the Related Art

There are many patients that require supplemental oxygen as part of Long Term Oxygen Therapy (LTOT). Currently, the vast majority of patients that are receiving LTOT are diagnosed under the general category of Chronic Obstructive Pulmonary Disease, COPD. This general diagnosis includes such common diseases as Chronic Asthma, Emphysema, Congestive Heart Failure and several other cardiopulmonary conditions. Other people (e.g., obese individuals) may also require supplemental oxygen, for example, to maintain elevated activity levels.

Doctors may prescribe oxygen concentrators or portable tanks of medical oxygen for these patients. Usually a specific oxygen flow rate is prescribed (e.g., 1 liter per minute (LPM), 2 LPM, 3 LPM, etc.). Experts in this field have also recognized that exercise for these patients provide long term benefits that slow the progression of the disease, improve quality of life and extend patient longevity. Most stationary forms of exercise like tread mills and stationary bicycles, however, are too strenuous for these patients. As a result, the need for mobility has long been recognized. Until recently, this mobility has been facilitated by the use of small compressed oxygen tanks. The disadvantage of these tanks is that they have a finite amount of oxygen and they are heavy, weighing about 50 pounds, when mounted on a cart with dolly wheels.

Oxygen concentrators have been in use for about 50 years to supply patients suffering from respiratory insufficiency with supplemental oxygen. Traditional oxygen concentrators used to provide these flow rates have been bulky and heavy making ordinary ambulatory activities with them difficult and impractical. Recently, companies that manufacture large stationary home oxygen concentrators began developing portable oxygen concentrators, POCs. The advantage of POCs concentrators was that they can produce a theoretically endless supply of oxygen. In order to make these devices small for mobility, the various systems necessary for the production of oxygen enriched gas are condensed.

SUMMARY

Systems and methods of providing an oxygen enriched gas to a user of an oxygen concentrator are described herein.

In one embodiment, a method of providing oxygen enriched gas to a user of an oxygen concentrator, includes: measuring the time between at least three successive breaths, wherein a breath is determined to begin when a drop in pressure is measured using a pressure sensor coupled to an outlet of a conduit coupling the user to an oxygen enriched gas source; determining an average breathing rate based on the time between each of the successive breaths, wherein the time between the penultimate breath and the last breath is not used to determine the average breathing rate; and setting an inspiration breath pressure threshold for the pressure sensor based on the determined average breathing rate. In an embodiment, the time is measured between six successive breaths. Adjusting the inspiration breath pressure threshold based on the average breathing rate, in some embodiments, is performed automatically. The oxygen enriched gas source may be an oxygen concentrator system or an oxygen tank.

In some embodiments, the threshold inspiration pressure is lowered when the determined average breathing rate changes from greater than 10 breaths per minute to less than 10 breaths per minute. In some embodiments, the threshold inspiration pressure is increased when the determined average breathing rate changes from less than 15 breaths per minute to greater than 15 breaths per minute. The inspiration breath pressure threshold may be maintained at a current setting when the average breathing rate is between about 10 breaths per minute and about 15 breaths per minute.

In some embodiments, the method further includes switching to an active mode, a sedentary mode, or remaining at the current mode based on the average breathing rate. For example, an active mode may be implemented when the average breathing rate comprises at least 15 breaths per minute. A sedentary mode may be activated when the average breathing rate comprises less than 10 breaths per minute.

In an embodiment, an oxygen concentrator apparatus includes: a pressure sensor, the pressure sensor configured to detect a breath pressure of a user; and a processor operable coupled to the pressure sensor. The processor is capable of executing non-transitory program instructions, wherein the program instructions are operable to: automatically measure the time between at least three successive breaths, wherein a breath is determined to begin when a drop in pressure is measured using the pressure sensor; determine an average breathing rate based on the time between each of the successive breaths, wherein the time between the penultimate breath and the last breath is not used to determine the average breathing rate; and set an inspiration breath pressure threshold for the pressure sensor based on the determined average breathing rate.

In an embodiment, a method of providing oxygen enriched gas to a user of an oxygen concentrator, includes: measuring the time between a plurality of successive breaths, wherein a breath is determined to begin when a drop in pressure is measured using a pressure sensor coupled to an outlet of a conduit coupling the user to an oxygen enriched gas source; determining an average time between each of the successive breaths, wherein the time between the penultimate breath and the last breath is not used to determine the average time; and setting an inspiration breath pressure threshold for the pressure sensor based on the determined average time, wherein the breath pressure threshold is set to an active mode breath pressure threshold if the average time is less than a predefined time, and wherein the breath pressure threshold is set to a sleep mode breath pressure threshold if the average time is greater than a predefined time, wherein the sleep mode breath pressure threshold is lower than the active mode breath pressure threshold; measuring the time since the penultimate breath and the time since the last breath when in sleep mode; and automatically providing oxygen enriched gas to the user if the sum of the time since the penultimate breath plus the time since the last breath is greater than a function of the determined average breathing time. Adjusting the inspiration breath pressure threshold, in an embodiment, is automatically based on the average time.

In some embodiments, the predefined time is between about 8 seconds and about 12 seconds. In some embodiments, the function of the determined average breathing time is a constant times the determined average breathing time, wherein the constant is between 1.5 and 2.5. The method also includes measuring the time since the penultimate breath, wherein if two breaths are not received within a predetermined time, a false breath time is added to the successive breaths and the average calculated. In one embodiment, the method includes measuring the time between at least six successive breaths, wherein the time between the $5^{th}$ breath and the $6^{th}$ breath is not used to determine the average time.

In an embodiment, automatically providing oxygen enriched gas comprises delivering oxygen enriched gas to the user every 3-4 seconds. In an embodiment, the time between each automatic delivery of oxygen enriched gas is varied randomly between 3-4 seconds. Alternatively, the time between each automatic delivery of oxygen enriched gas is varied by a constant amount, cycling between 3-4 seconds. The automatic delivery of oxygen enriched gas to the user is discontinued if a breath is detected from the user.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
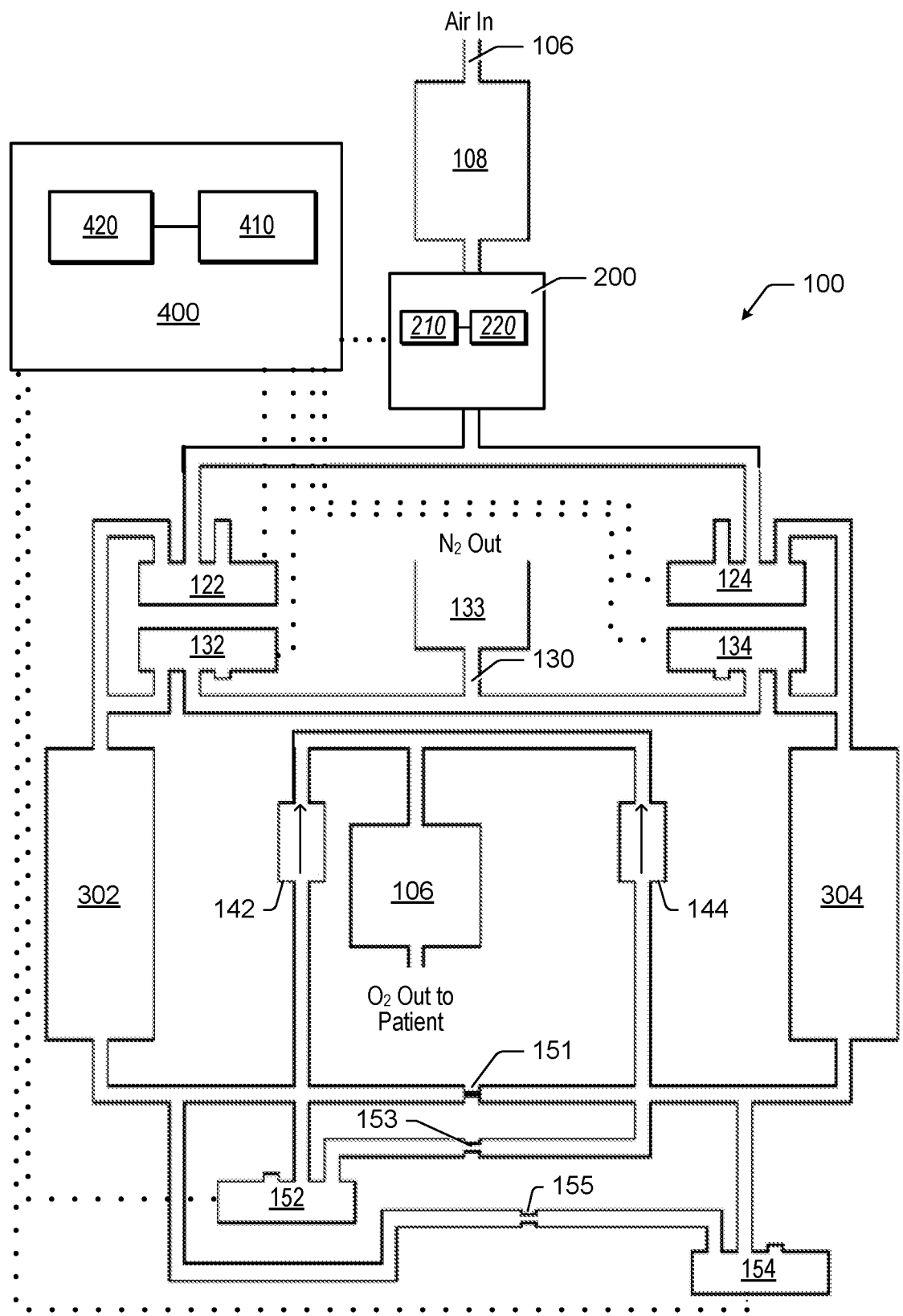
FIG. 1 depicts a schematic diagram of an embodiment of the components of an oxygen concentrator.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims.

DETAILED DESCRIPTION

It is to be understood the present invention is not limited to particular devices or methods, which may, of course, vary. It is also to be understood that the terminology used herein is for the purpose of describing particular embodiments only, and is not intended to be limiting. Headings are for organizational purposes only and are not meant to be used to limit or interpret the description or claims. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to."

The term "coupled" as used herein means either a direct connection or an indirect connection (e.g., one or more intervening connections) between one or more objects or components. The phrase "connected" means a direct connection between objects or components such that the objects or components are connected directly to each other. As used herein the phrase "obtaining" a device means that the device is either purchased or constructed.

Oxygen concentrators take advantage of pressure swing adsorption (PSA). Pressure swing adsorption involves using a compressor to increase gas pressure inside a canister that contains particles of a gas separation adsorbent. As the pressure increases, certain molecules in the gas may become adsorbed onto the gas separation adsorbent. Removal of a portion of the gas in the canister under the pressurized conditions allows separation of the non-adsorbed molecules from the adsorbed molecules. The gas separation adsorbent may be regenerated by reducing the pressure, which reverses the adsorption of molecules from the adsorbent. Further details regarding oxygen concentrators may be found, for example, in U.S. Published Patent Application No. 2009-0065007, published Mar. 12, 2009, and entitled "Oxygen Concentrator Apparatus and Method", which is incorporated herein by reference.

Ambient air usually includes approximately 78% nitrogen and 21% oxygen with the balance comprised of argon, carbon dioxide, water vapor and other trace elements. If a gas mixture such as air, for example, is passed under pressure through a vessel containing a gas separation adsorbent bed that attracts nitrogen more strongly than it does oxygen, part or all of the nitrogen will stay in the bed, and the gas coming out of the vessel will be enriched in oxygen. When the bed reaches the end of its capacity to adsorb nitrogen, it can be regenerated by reducing the pressure, thereby releasing the adsorbed nitrogen. It is then ready for another cycle of producing oxygen enriched air. By alternating canisters in a two-canister system, one canister can be collecting oxygen while the other canister is being purged (resulting in a continuous separation of the oxygen from the nitrogen). In this manner, oxygen can be accumulated out of the air for a variety of uses include providing supplemental oxygen to patients.

FIG. 1 illustrates a schematic diagram of an oxygen concentrator 100, according to an embodiment. Oxygen concentrator 100 may concentrate oxygen out of an air stream to provide oxygen enriched gas to a user. As used herein, "oxygen enriched gas" is composed of at least about 50% oxygen, at least about 60% oxygen, at least about 70% oxygen, at least about 80% oxygen, at least about 90% oxygen, at least about 95% oxygen, at least about 98% oxygen, or at least about 99% oxygen.

Oxygen concentrator 100 may be a portable oxygen concentrator. For example, oxygen concentrator 100 may have a weight and size that allows the oxygen concentrator to be carried by hand and/or in a carrying case. In one embodiment, oxygen concentrator 100 has a weight of less than about 20 lbs., less than about 15 lbs., less than about 10 lbs., or less than about 5 lbs. In an embodiment, oxygen concentrator 100 has a volume of less than about 1000 cubic inches, less than about 750 cubic inches; less than about 500 cubic inches, less than about 250 cubic inches, or less than about 200 cubic inches.

Oxygen may be collected from ambient air by pressurizing ambient air in canisters 302 and 304, which include a gas separation adsorbent. Gas separation adsorbents useful in an oxygen concentrator are capable of separating at least nitrogen from an air stream to produce oxygen enriched gas. Examples of gas separation adsorbents include molecular sieves that are capable of separation of nitrogen from an air stream. Examples of adsorbents that may be used in an oxygen concentrator include, but are not limited to, zeolites (natural) or synthetic crystalline aluminosilicates that separate nitrogen from oxygen in an air stream under elevated pressure. Examples of synthetic crystalline aluminosilicates that may be used include, but are not limited to: OXYSIV adsorbents available from UOP LLC, Des Plaines, Iowa; SYLOBEAD adsorbents available from W. R. Grace & Co, Columbia, Md.; SILIPORITE adsorbents available from CECA S.A. of Paris, France; ZEOCHEM adsorbents available from Zeochem AG, Uetikon, Switzerland; and AgLi-LSX adsorbent available from Air Products and Chemicals, Inc., Allentown, Pa.

As shown in FIG. 1, air may enter the oxygen concentrator through air inlet 106. Air may be drawn into air inlet 106 by compression system 200. Compression system 200 may draw in air from the surroundings of the oxygen concentrator and compress the air, forcing the compressed air into one or both canisters 302 and 304. In an embodiment, an inlet muffler 108 may be coupled to air inlet 106 to reduce sound produced by air being pulled into the oxygen generator by compression system 200. In an embodiment, inlet muffler 108 may be a moisture and sound absorbing muffler. For example, a water absorbent material (such as a polymer water absorbent material or a zeolite material) may be used to both absorb water from the incoming air and to reduce the sound of the air passing into the air inlet 106.

Compression system 200 may include one or more compressors capable of compressing air. In some embodiments, compression system may include one, two, three, four, or more compressors. Compression system 200 as depicted that includes compressor 210 and motor 220. Motor 220 is coupled to compressor 210 and provides an operating force to the compressor to operate the compression mechanism. Pressurized air, produced by compression system 200, may be forced into one or both of the canisters 302 and 304. In some embodiments, the ambient air may be pressurized in the canisters to a pressure approximately in a range of 13-20 pounds per square inch (psi). Other pressures may also be used, depending on the type of gas separation adsorbent disposed in the canisters.

In some embodiments, motor 220 is coupled to a pressurizing device (e.g. piston pump or a diaphragm pump). The pressuring device may be a piston pump that has multiple pistons. During operation, the pistons may be selectively turned on or off. In some embodiments, motor 220 may be coupled to multiple pumps. Each pump may be selectively turned on or off. For example, controller 400 may determine which pumps or pistons should be operated based on predetermined operating conditions.

Coupled to each canister 302/304 are inlet valves 122/124 and outlet valves 132/134. As shown in FIG. 1, inlet valve 122 is coupled to canister 302 and inlet valve 124 is coupled to canister 304. Outlet valve 132 is coupled to canister 302 and outlet valve 134 is coupled to canister 304. Inlet valves 122/124 are used to control the passage of air from compression system 200 to the respective canisters. Outlet valves 132/134 are used to release gas from the respective canisters during a venting process. In some embodiments, inlet valves 122/124 and outlet valves 132/134 may be silicon plunger solenoid valves. Other types of valves, however, may be used. Plunger valves offer advantages over other kinds of valves by being quiet and having low slippage.

In some embodiments, a two-step valve actuation voltage may be used to control inlet valves 122/124 and outlet valves 132/134. For example, a high voltage (e.g., 24 V) may be applied to an inlet valve to open the inlet valve. The voltage may then be reduced (e.g., to 7 V) to keep the inlet valve open. Using less voltage to keep a valve open may use less power (Power=Voltage*Current). This reduction in voltage minimizes heat buildup and power consumption to extend run time from the battery. When the power is cut off to the valve, it closes by spring action. In some embodiments, the voltage may be applied as a function of time that is not necessarily a stepped response (e.g., a curved downward voltage between an initial 24 V and a final 7 V).

In some embodiments, air may be pulled into the oxygen concentrator through compressors 305, 310. In some embodiments, air may flow from compressors 305, 310 to canisters 302, 304. In some embodiments, one of valves 122 or 124 may be closed (e.g., as signaled by controller 400) resulting in the combined output of both compressors 305, 310 lowing through the other respective valve 122 or 124 into a respective canister 302, 304. For example, if valve 124 is closed, the air from both compressors 305, 310 may flow through valve 122. If valve 122 is closed, the air from both compressors 305, 310 may flow through valve 124. In some embodiments, valve 122 and valve 124 may alternate to alternately direct the air from the compressors 305, 310 into respective canisters 302 or 304.

In an embodiment, pressurized air is sent into one of canisters 302 or 304 while the other canister is being vented. For example, during use, inlet valve 122 is opened while inlet valve 124 is closed. Pressurized air from compression system 200 is forced into canister 302, while being inhibited from entering canister 304 by inlet valve 124. In an embodiment, a controller 400 is electrically coupled to valves 122, 124, 132, and 134. Controller 400 includes one or more processors 410 operable to execute program instructions stored in memory 420. The program instructions are operable to perform various predefined methods that are used to operate the oxygen concentrator. Controller 400 may include program instructions for operating inlet valves 122 and 124 out of phase with each other, i.e., when one of inlet valves 122 or 124 is opened, the other valve is closed. During pressurization of canister 302, outlet valve 132 is closed and outlet valve 134 is opened. Similar to the inlet valves, outlet valves 132 and 134 are operated out of phase with each other. In some embodiments, the voltages and the duration of the voltages used to open the input and output valves may be controlled by controller 400.

Check valves 142 and 144 are coupled to canisters 302 and 304, respectively. Check valves 142 and 144 are one way valves that are passively operated by the pressure differentials that occur as the canisters are pressurized and vented. Check valves 142 and 144 are coupled to canisters to allow oxygen produced during pressurization of the canister to flow out of the canister, and to inhibit back flow of oxygen or any other gases into the canister. In this manner, check valves 142 and 144 act as one way valves allowing oxygen enriched gas to exit the respective canister during pressurization.

The term "check valve", as used herein, refers to a valve that allows flow of a fluid (gas or liquid) in one direction and inhibits back flow of the fluid. Examples of check valves that are suitable for use include, but are not limited to: a ball check valve; a diaphragm check valve; a butterfly check valve; a swing check valve; a duckbill valve; and a lift check valve. Under pressure, nitrogen molecules in the pressurized ambient air are adsorbed by the gas separation adsorbent in the pressurized canister. As the pressure increases, more nitrogen is adsorbed until the gas in the canister is enriched in oxygen. The nonadsorbed gas molecules (mainly oxygen) flow out of the pressurized canister when the pressure reaches a point sufficient to overcome the resistance of the check valve coupled to the canister. In one embodiment, the pressure drop of the check valve in the forward direction is less than 1 psi. The break pressure in the reverse direction is greater than 100 psi. It should be understood, however, that modification of one or more components would alter the operating parameters of these valves. If the forward flow pressure is increased, there is, generally, a reduction in oxygen enriched gas production. If the break pressure for reverse flow is reduced or set too low, there is, generally, a reduction in oxygen enriched gas pressure.

In an exemplary embodiment, canister 302 is pressurized by compressed air produced in compression system 200 and passed into canister 302. During pressurization of canister 302 inlet valve 122 is open, outlet valve 132 is closed, inlet valve 124 is closed and outlet valve 134 is open. Outlet valve 134 is opened when outlet valve 132 is closed to allow substantially simultaneous venting of canister 304 while canister 302 is pressurized. Canister 302 is pressurized until the pressure in canister is sufficient to open check valve 142. Oxygen enriched gas produced in canister 302 exits through check valve and, in one embodiment, is collected in accumulator 106.

After some time the gas separation adsorbent will become saturated with nitrogen and will be unable to separate significant amounts of nitrogen from incoming air. This point is usually reached after a predetermined time of oxygen enriched gas production. In the embodiment described above, when the gas separation adsorbent in canister 302 reaches this saturation point, the inflow of compressed air is stopped and canister 302 is vented to remove nitrogen. During venting, inlet valve 122 is closed, and outlet valve 132 is opened. While canister 302 is being vented, canister 304 is pressurized to produce oxygen enriched gas in the same manner described above. Pressurization of canister 304 is achieved by closing outlet valve 134 and opening inlet valve 124. The oxygen enriched gas exits canister 304 through check valve 144.

During venting of canister 302, outlet valve 132 is opened allowing pressurized gas (mainly nitrogen) to exit the canister through concentrator outlet 130. In an embodiment, the vented gases may be directed through muffler 133 to reduce the noise produced by releasing the pressurized gas from the canister. As gas is released from canister 302, pressure in the canister drops. The drop in pressure may allow the nitrogen to become desorbed from the gas separation adsorbent. The released nitrogen exits the canister through outlet 130, resetting the canister to a state that allows renewed separation of oxygen from an air stream. Muffler 133 may include open cell foam (or another material) to muffle the sound of the gas leaving the oxygen concentrator. In some embodiments, the combined muffling components/techniques for the input of air and the output of gas may provide for oxygen concentrator operation at a sound level below 50 decibels.

During venting of the canisters, it is advantageous that at least a majority of the nitrogen is removed. In an embodiment, at least about 50%, at least about 60%, at least about 70%, at least about 80%, at least about 90%, at least about 95%, at least about 98%, or substantially all of the nitrogen in a canister is removed before the canister is re-used to separate oxygen from air. In some embodiments, a canister may be further purged of nitrogen using an oxygen enriched stream that is introduced into the canister from the other canister.

In an exemplary embodiment, a portion of the oxygen enriched gas may be transferred from canister 302 to canister 304 when canister 304 is being vented of nitrogen. Transfer of oxygen enriched gas from canister 302 to 304, during venting of canister 304, helps to further purge nitrogen (and other gases) from the canister. In an embodiment, oxygen enriched gas may travel through flow restrictors 151, 153, and 155 between the two canisters. Flow restrictor 151 may be a trickle flow restrictor. Flow restrictor 151, for example, may be a 0.009 D flow restrictor (e.g., the flow restrictor has a radius of 0.009 inches which is less than the diameter of the tube it is inside). Flow restrictors 153 and 155 may be 0.013 D flow restrictors. Other flow restrictor types and sizes are also contemplated and may be used depending on the specific configuration and tubing used to couple the canisters. In some embodiments, the flow restrictors may be press fit flow restrictors that restrict air flow by introducing a narrower diameter in their respective tube. In some embodiments, the press fit flow restrictors may be made of sapphire, metal or plastic (other materials are also contemplated).

Flow of oxygen enriched gas is also controlled by use of valve 152 and valve 154. Valves 152 and 154 may be opened for a short duration during the venting process (and may be closed otherwise) to prevent excessive oxygen loss out of the purging canister. Other durations are also contemplated. In an exemplary embodiment, canister 302 is being vented and it is desirable to purge canister 302 by passing a portion of the oxygen enriched gas being produced in canister 304 into canister 302. A portion of oxygen enriched gas, upon pressurization of canister 304, will pass through flow restrictor 151 into canister 302 during venting of canister 302. Additional oxygen enriched air is passed into canister 302, from canister 304, through valve 154 and flow restrictor 155. Valve 152 may remain closed during the transfer process, or may be opened if additional oxygen enriched gas is needed. The selection of appropriate flow restrictors 151 and 155, coupled with controlled opening of valve 154 allows a controlled amount of oxygen enriched gas to be sent from canister 304 to 302. In an embodiment, the controlled amount of oxygen enriched gas is an amount sufficient to purge canister 302 and minimize the loss of oxygen enriched gas through venting valve 132 of canister 302. While this embodiment describes venting of canister 302, it should be understood that the same process can be used to vent canister 304 using flow restrictor 151, valve 152 and flow restrictor 153.

The pair of equalization/vent valves 152/154 work with flow restrictors 153 and 155 to optimize the air flow balance between the two canisters. This may allow for better flow control for venting the canisters with oxygen enriched gas from the other of the canisters. It may also provide better flow direction between the two canisters. It has been found that, while flow valves 152/154 may be operated as bi-directional valves, the flow rate through such valves varies depending on the direction of fluid flowing through the valve. For example, oxygen enriched gas flowing from canister 304 toward canister 302 has a flow rate faster through valve 152 than the flow rate of oxygen enriched gas flowing from canister 302 toward canister 304 through valve 152. If a single valve was to be used, eventually either too much or too little oxygen enriched gas would be sent between the canisters and the canisters would, over time, begin to produce different amounts of oxygen enriched gas. Use of opposing valves and flow restrictors on parallel air pathways may equalize the flow pattern of the oxygen between the two canisters. Equalizing the flow may allow for a steady amount of oxygen available to the user over multiple cycles and also may allow a predictable volume of oxygen to purge the other of the canisters. In some embodiments, the air pathway may not have restrictors but may instead have a valve with a built in resistance or the air pathway itself may have a narrow radius to provide resistance.

At times, oxygen concentrator may be shut down for a period of time. When an oxygen concentrator is shut down, the temperature inside the canisters may drop as a result of the loss of adiabatic heat from the compression system. As the temperature drops, the volume occupied by the gases inside the canisters will drop. Cooling of the canisters may lead to a negative pressure in the canisters. Valves (e.g., valves 122, 124, 132, and 134) leading to and from the canisters are dynamically sealed rather than hermetically sealed. Thus, outside air may enter the canisters after shutdown to accommodate the pressure differential. When outside air enters the canisters, moisture from the outside air may condense inside the canister as the air cools. Condensation of water inside the canisters may lead to gradual degradation of the gas separation adsorbents, steadily reducing ability of the gas separation adsorbents to produce oxygen enriched gas.

In an embodiment, outside air may be inhibited from entering canisters after the oxygen concentrator is shut down by pressurizing both canisters prior to shut down. By storing the canisters under a positive pressure, the valves may be forced into a hermetically closed position by the internal pressure of the air in the canisters. In an embodiment, the pressure in the canisters, at shutdown, should be at least greater than ambient pressure. As used herein the term "ambient pressure" refers to the pressure of the surroundings that the oxygen generator is located (e.g. the pressure inside a room, outside, in a plane, etc.). In an embodiment, the pressure in the canisters, at shutdown, is at least greater than standard atmospheric pressure (i.e., greater than 760 mmHg (Torr), 1 atm, 101,325 Pa). In an embodiment, the pressure in the canisters, at shutdown, is at least about 1.1 times greater than ambient pressure; is at least about 1.5 times greater than ambient pressure; or is at least about 2 times greater than ambient pressure.

In an embodiment, pressurization of the canisters may be achieved by directing pressurized air into each canister from the compression system and closing all valves to trap the pressurized air in the canisters. In an exemplary embodiment, when a shutdown sequence is initiated, inlet valves 122 and 124 are opened and outlet valves 132 and 134 are closed. Because inlet valves 122 and 124 are joined together by a common conduit, both canisters 302 and 304 may become pressurized as air and or oxygen enriched gas from one canister may be transferred to the other canister. This situation may occur when the pathway between the compression system and the two inlet valves allows such transfer. Because the oxygen generator operates in an alternating pressurize/venting mode, at least one of the canisters should be in a pressurized state at any given time. In an alternate embodiment, the pressure may be increased in each canister by operation of compression system 200. When inlet valves 122 and 124 are opened, pressure between canisters 302 and 304 will equalize, however, the equalized pressure in either canister may not be sufficient to inhibit air from entering the canisters during shutdown. In order to ensure that air is inhibited from entering the canisters, compression system 200 may be operated for a time sufficient to increase the pressure inside both canisters to a level at least greater than ambient pressure. Regardless of the method of pressurization of the canisters, once the canisters are pressurized, inlet valves 122 and 124 are closed, trapping the pressurized air inside the canisters, which inhibits air from entering the canisters during the shutdown period.

An outlet system, coupled to one or more of the canisters, includes one or more conduits for providing oxygen enriched gas to a user. In an embodiment, oxygen enriched gas produced in either of canisters 302 and 304 is collected in accumulator 106 through check valves 142 and 144, respectively, as depicted schematically in FIG. 1. The oxygen enriched gas leaving the canisters may be collected in oxygen accumulator 106 prior to being provided to a user. In some embodiments, a tube may be coupled to accumulator 106 to provide the oxygen enriched gas to the user. Oxygen enriched gas may be provided to the user through an airway delivery device that transfer the oxygen enriched gas to the user's mouth and/or nose. In an embodiment, an outlet may include a tube that directs the oxygen toward a user's nose and/or mouth that may not be directly coupled to the user's nose.

Figure 2:
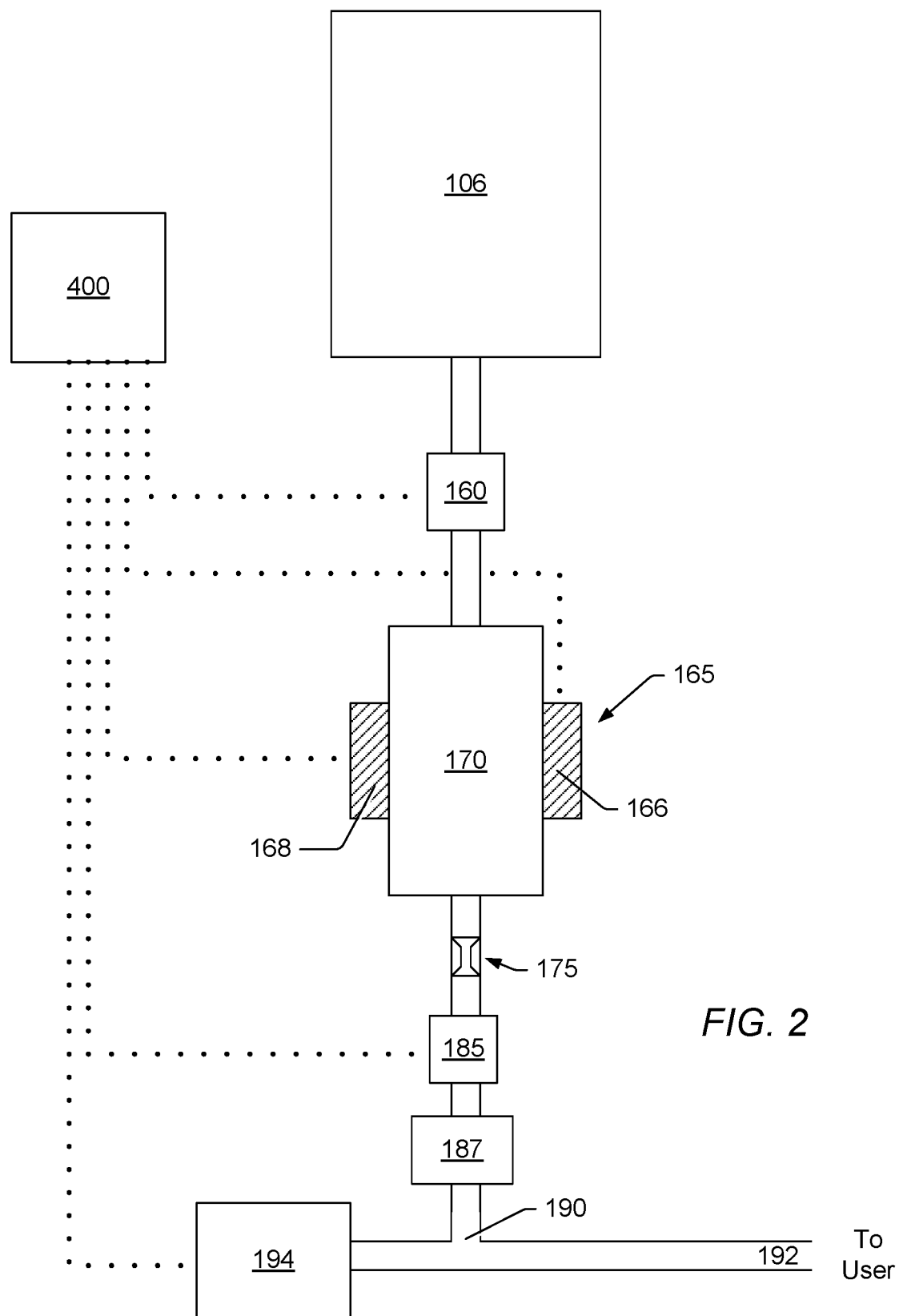
FIG. 2 depicts a schematic diagram of an embodiment of the outlet components of an oxygen concentrator.

Turning to FIG. 2, a schematic diagram of an embodiment of an outlet system for an oxygen concentrator is shown. Supply valve 160 may be coupled to outlet tube to control the release of the oxygen enriched gas from accumulator 106 to the user. In an embodiment, supply valve 160 is an electromagnetically actuated plunger valve. Supply valve 160 is actuated by controller 400 to control the delivery of oxygen enriched gas to a user. Actuation of supply valve 160 is not timed or synchronized to the pressure swing adsorption process. Instead, actuation is, in some embodiments, synchronized to the patient's breathing. Additionally, supply valve 160 may have multiple actuations to help establish a clinically effective flow profile for providing oxygen enriched gas.

Oxygen enriched gas in accumulator 106 passes through supply valve 160 into expansion chamber 170 as depicted in FIG. 2. In an embodiment, expansion chamber may include one or more devices capable of being used to determine an oxygen concentration of gas passing through the chamber. Oxygen enriched gas in expansion chamber 170 builds briefly, through release of gas from accumulator by supply valve 160, and then is bled through small orifice flow restrictor 175 to flow rate sensor 185 and then to particulate filter 187. Flow restrictor 175 may be a 0.025 D flow restrictor. Other flow restrictor types and sizes may be used. In some embodiments, the diameter of the air pathway in the housing may be restricted to create restricted air flow. Flow rate sensor 185 may be any sensor capable of assessing the rate of gas flowing through the conduit. Particulate filter 187 may be used to filter bacteria, dust, granule particles, etc. prior to delivery of the oxygen enriched gas to the user. The oxygen enriched gas passes through filter 187 to connector 190 which sends the oxygen enriched gas to the user via conduit 192 and to pressure sensor 194.

The fluid dynamics of the outlet pathway, coupled with the programmed actuations of supply valve 160, results in a bolus of oxygen being provided at the correct time and with a flow profile that assures rapid delivery into the patient's lungs without any excessive flow rates that would result in wasted retrograde flow out the nostrils and into the atmosphere. It has been found, in our specific system, that the total volume of the bolus required for prescriptions is equal to 11 mL for each LPM, i.e., 11 mL for a prescription of 1 LPM; 22 mL for a prescription of 2 LPM; 33 mL for a prescription of 3 LPM; 44 mL for a prescription of 4 LPM; 55 mL for a prescription of 5 LPM; etc. This is generally referred to as the LPM equivalent. It should be understood that the LPM equivalent may vary between apparatus due to differences in construction design, tubing size, chamber size, etc.

Expansion chamber 170 may include one or more oxygen sensors capable of being used to determine an oxygen concentration of gas passing through the chamber. In an embodiment, the oxygen concentration of gas passing through expansion chamber 170 is assessed using oxygen sensor 165. An oxygen sensor is a device capable of detecting oxygen in a gas. Examples of oxygen sensors include, but are not limited to, ultrasonic oxygen sensors, electrical oxygen sensors, and optical oxygen sensors. In one embodiment, oxygen sensor 165 is an ultrasonic oxygen sensor that includes ultrasonic emitter 166 and ultrasonic receiver 168. In some embodiments, ultrasonic emitter 166 may include multiple ultrasonic emitters and ultrasonic receiver 168 may include multiple ultrasonic receivers. In embodiments having multiple emitters/receivers, the multiple ultrasonic emitters and multiple ultrasonic receivers may be axially aligned (e.g., across the gas mixture flow path which may be perpendicular to the axial alignment).

In use, an ultrasonic sound wave (from emitter 166) may be directed through oxygen enriched gas disposed in chamber 170 to receiver 168. Ultrasonic sensor assembly may be based on detecting the speed of sound through the gas mixture to determine the composition of the gas mixture (e.g., the speed of sound is different in nitrogen and oxygen). In a mixture of the two gases, the speed of sound through the mixture may be an intermediate value proportional to the relative amounts of each gas in the mixture. In use, the sound at the receiver 168 is slightly out of phase with the sound sent from emitter 166. This phase shift is due to the relatively slow velocity of sound through a gas medium as compared with the relatively fast speed of the electronic pulse through wire. The phase shift, then, is proportional to the distance between the emitter and the receiver and the speed of sound through the expansion chamber. The density of the gas in the chamber affects the speed of sound through the chamber and the density is proportional to the ratio of oxygen to nitrogen in the chamber. Therefore, the phase shift can be used to measure the concentration of oxygen in the expansion chamber. In this manner the relative concentration of oxygen in the accumulation chamber may be assessed as a function of one or more properties of a detected sound wave traveling through the accumulation chamber.

In some embodiments, multiple emitters 166 and receivers 168 may be used. The readings from the emitters 166 and receivers 168 may be averaged to cancel errors that may be inherent in turbulent flow systems. In some embodiments, the presence of other gases may also be detected by measuring the transit time and comparing the measured transit time to predetermined transit times for other gases and/or mixtures of gases.

The sensitivity of the ultrasonic sensor system may be increased by increasing the distance between emitter 166 and receiver 168, for example to allow several sound wave cycles to occur between emitter 166 and the receiver 168. In some embodiments, if at least two sound cycles are present, the influence of structural changes of the transducer may be reduced by measuring the phase shift relative to a fixed reference at two points in time. If the earlier phase shift is subtracted from the later phase shift, the shift caused by thermal expansion of expansion chamber 170 may be reduced or cancelled. The shift caused by a change of the distance between emitter 166 and receiver 168 may be the approximately the same at the measuring intervals, whereas a change owing to a change in oxygen concentration may be cumulative. In some embodiments, the shift measured at a later time may be multiplied by the number of intervening cycles and compared to the shift between two adjacent cycles. Further details regarding sensing of oxygen in the expansion chamber may be found, for example, in U.S. Published Patent Application No. 2009-0065007, published Mar. 12, 2009, and entitled "Oxygen Concentrator Apparatus and Method, which is incorporated herein by reference.

Flow rate sensor 185 may be used to determine the flow rate of gas flowing through the outlet system. Flow rate sensors that may be used include, but are not limited to: diaphragm/bellows flow meters; rotary flow meters (e.g. Hall Effect flow meters); turbine flow meters; orifice flow meters; and ultrasonic flow meters. Flow rate sensor 185 may be coupled to controller 400. The rate of gas flowing through the outlet system may be an indication of the breathing volume of the user. Changes in the flow rate of gas flowing through the outlet system may also be used to determine a breathing rate of the user. Controller 400 may control actuation of supply valve 160 based on the breathing rate and/or breathing volume of the user, as assessed by flow rate sensor 185

In some embodiments, ultrasonic sensor system 165 and, for example, flow rate sensor 185 may provide a measurement of an actual amount of oxygen being provided. For example, follow rate sensor 185 may measure a volume of gas (based on flow rate) provided and ultrasonic sensor system 165 may provide the concentration of oxygen of the gas provided. These two measurements together may be used by controller 400 to determine an approximation of the actual amount of oxygen provided to the user.

Oxygen enriched gas passes through flow meter 185 to filter 187. Filter 187 removes bacteria, dust, granule particles, etc. prior to providing the oxygen enriched gas to the user. The filtered oxygen enriched gas passes through filter 187 to connector 190. Connector 190 may be a "Y" connector coupling the outlet of filter 187 to pressure sensor 194 and outlet conduit 192. Pressure sensor 194 may be used to monitor the pressure of the gas passing through conduit 192 to the user. Changes in pressure, sensed by pressure sensor 194, may be used to determine a breathing rate of a user, as well as the onset of inhalation. Controller 400 may control actuation of supply valve 160 based on the breathing rate and/or onset of inhalation of the user, as assessed by pressure sensor 194. In an embodiment, controller 400 may control actuation of supply valve 160 based on information provided by flow rate sensor 185 and pressure sensor 194.

Figure 3:
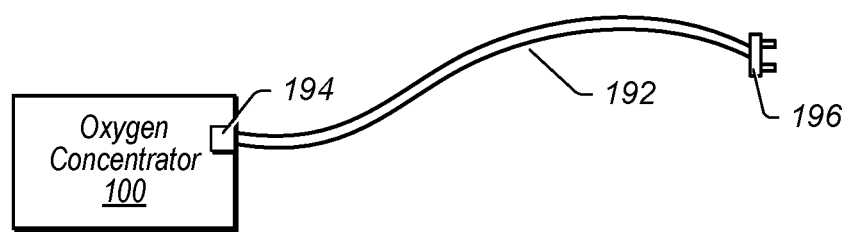
FIG. 3 depicts a schematic diagram of an embodiment of an outlet conduit for an oxygen concentrator.

Oxygen enriched gas may be provided to a user through conduit 192. In an embodiment, conduit 192 may be a silicone tube. Conduit 192 may be coupled to a user using an airway coupling member 196, as depicted in FIG. 3. Airway coupling member 196 may be any device capable of providing the oxygen enriched gas to nasal cavities or oral cavities. Examples of airway coupling members include, but are not limited to: nasal masks, nasal pillows, nasal prongs, nasal cannulas, and mouthpieces. A nasal cannula airway delivery device is depicted in FIG. 3. During use, oxygen enriched gas from oxygen concentrator system 100 is provided to the user through conduit 192 and airway coupling member 196. Airway coupling member 196 is positioned proximate to a user's airway (e.g., proximate to the user's mouth and or nose) to allow delivery of the oxygen enriched gas to the user while allowing the user to breath air from the surroundings.

Canister System

Figure 4:
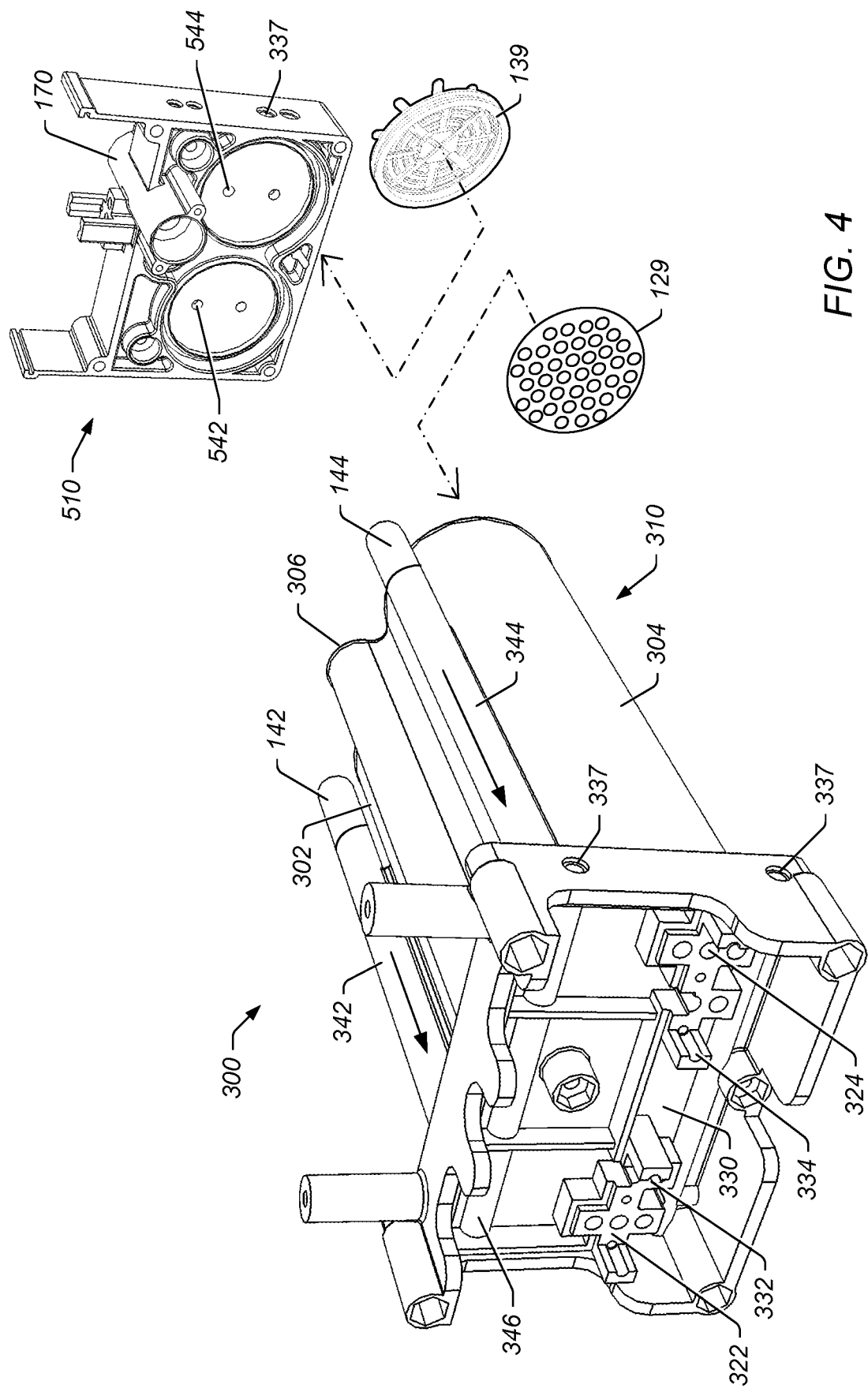
FIG. 4 depicts a perspective view of an embodiment of a dissembled canister system.

Oxygen concentrator system 100 may include at least two canisters, each canister including a gas separation adsorbent. The canisters of oxygen concentrator system 100 may be disposed formed from a molded housing. In an embodiment, canister system 300 includes two housing components 310 and 510, as depicted in FIG. 4. The housing components 310 and 510 may be formed separately and then coupled together. In some embodiments, housing components 310 and 510 may be injection molded or compression molded. Housing components 310 and 510 may be made from a thermoplastic polymer such as polycarbonate, methylene carbide, polystyrene, acrylonitrile butadiene styrene (ABS), polypropylene, polyethylene, or polyvinyl chloride. In another embodiment, housing components 310 and 510 may be made of a thermoset plastic or metal (such as stainless steel or a light-weight aluminum alloy). Lightweight materials may be used to reduce the weight of the oxygen concentrator 100. In some embodiments, the two housings 310 and 510 may be fastened together using screws or bolts. Alternatively, housing components 310 and 510 may be solvent welded together.

As shown, valve seats 320, 322, 324, and 326 and air pathways 330 and 332 may be integrated into the housing component 310 to reduce the number of sealed connections needed throughout the air flow of the oxygen concentrator 100. In various embodiments, the housing components 310 and 410 of the oxygen concentrator 100 may form a two-part molded plastic frame that defines two canisters 302 and 304 and accumulation chamber 106.

Air pathways/tubing between different sections in housing components 310 and 510 may take the form of molded conduits. Conduits in the form of molded channels for air pathways may occupy multiple planes in housing components 310 and 510. For example, the molded air conduits may be formed at different depths and at different x, y, z positions in housing components 310 and 510. In some embodiments, a majority or substantially all of the conduits may be integrated into the housing components 310 and 510 to reduce potential leak points.

In some embodiments, prior to coupling housing components 310 and 510 together, O-rings may be placed between various points of housing components 310 and 510 to ensure that the housing components are properly sealed. In some embodiments, components may be integrated and/or coupled separately to housing components 310 and 510. For example, tubing, flow restrictors (e.g., press fit flow restrictors), oxygen sensors, gas separation adsorbents 139, check valves, plugs, processors, power supplies, etc. may be coupled to housing components 510 and 410 before and/or after the housing components are coupled together.

In some embodiments, apertures 337 leading to the exterior of housing components 310 and 410 may be used to insert devices such as flow restrictors. Apertures may also be used for increased moldability. One or more of the apertures may be plugged after molding (e.g., with a plastic plug). In some embodiments, flow restrictors may be inserted into passages prior to inserting plug to seal the passage. Press fit flow restrictors may have diameters that may allow a friction fit between the press fit flow restrictors and their respective apertures. In some embodiments, an adhesive may be added to the exterior of the press fit flow restrictors to hold the press fit flow restrictors in place once inserted. In some embodiments, the plugs may have a friction fit with their respective tubes (or may have an adhesive applied to their outer surface). The press fit flow restrictors and/or other components may be inserted and pressed into their respective apertures using a narrow tip tool or rod (e.g., with a diameter less than the diameter of the respective aperture). In some embodiments, the press fit flow restrictors may be inserted into their respective tubes until they abut a feature in the tube to halt their insertion. For example, the feature may include a reduction in radius. Other features are also contemplated (e.g., a bump in the side of the tubing, threads, etc.). In some embodiments, press fit flow restrictors may be molded into the housing components (e.g., as narrow tube segments).

In some embodiments, spring baffle 129 may be placed into respective canister receiving portions of housing component 310 and M0 with the spring side of the baffle 129 facing the exit of the canister. Spring baffle 129 may apply force to gas separation adsorbent 139 in the canister while also assisting in preventing gas separation adsorbent 139 from entering the exit apertures. Use of a spring baffle 129 may keep the gas separation adsorbent compact while also allowing for expansion (e.g., thermal expansion). Keeping the gas separation adsorbent 139 compact may prevent the gas separation adsorbent from breaking during movement of the oxygen concentrator system 100).

Figure 5:
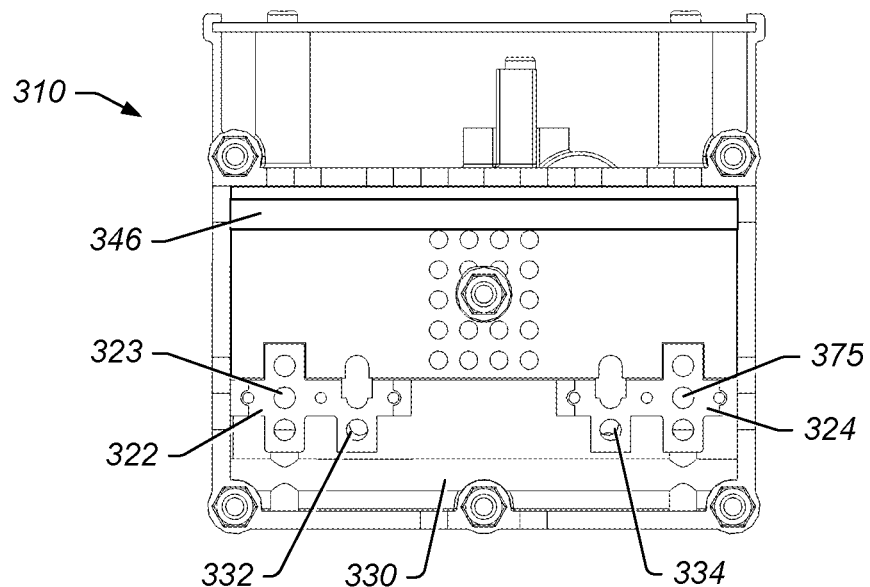
FIG. 5 depicts a perspective view of an embodiment of an end of a canister system.
Figure 6:
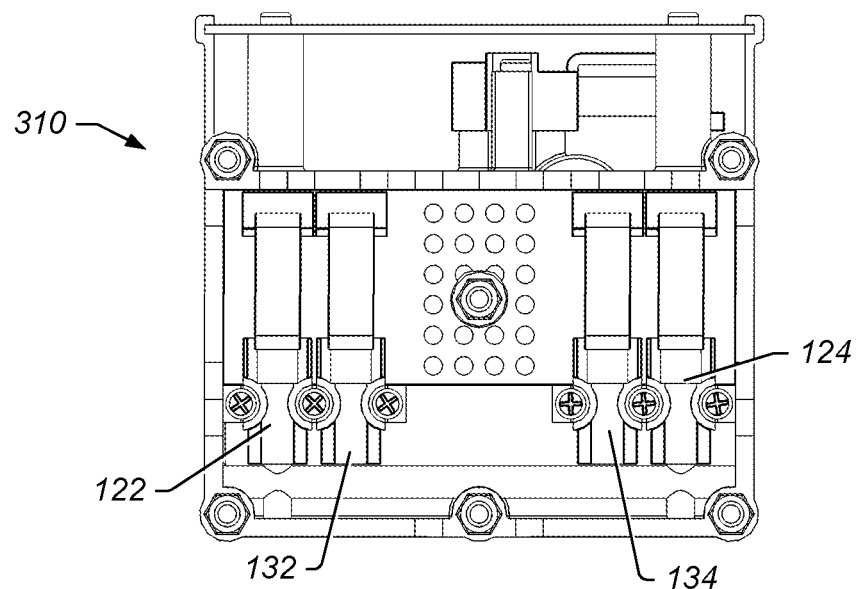
FIG. 6 depicts the assembled end of an embodiment of the canister system end depicted in FIG. 5.

In some embodiments, pressurized air from the compression system 200 may enter air inlet 306. Air inlet 306 is coupled to inlet conduit 330. Air enters housing component 310 through inlet 306 travels through conduit 330, and then to valve seats 322 and 324. FIG. 5 and FIG. 6 depict an end view of housing 310. FIG. 5, depicts an end view of housing 310 prior to fitting valves to housing 310. FIG. 6 depicts an end view of housing 310 with the valves fitted to the housing 310. Valve seats 322 and 324 are configured to receive inlet valves 122 and 124 respectively. Inlet valve 122 is coupled to canister 302 and inlet valve 124 is coupled to canister 304. Housing 310 also includes valve seats 332 and 334 configured to receive outlet valves 132 and 134 respectively. Outlet valve 132 is coupled to canister 302 and outlet valve 134 is coupled to canister 304. Inlet valves 122/124 are used to control the passage of air from conduit 330 to the respective canisters.

In an embodiment, pressurized air is sent into one of canisters 302 or 304 while the other canister is being vented. For example, during use, inlet valve 122 is opened while inlet valve 124 is closed. Pressurized air from compression system 200 is forced into canister 302, while being inhibited from entering canister 304 by inlet valve 124. During pressurization of canister 302, outlet valve 132 is closed and outlet valve 134 is opened. Similar to the inlet valves, outlet valves 132 and 134 are operated out of phase with each other. Each inlet valve seat 322 includes an opening 375 that passes through housing 310 into canister 302. Similarly valve seat 324 includes an opening 325 that passes through housing 310 into canister 302. Air from conduit 330 passes through openings 323, or 325 if the respective valve (322 or 324) is open, and enters a canister.

Check valves 142 and 144 (See, FIG. 4) are coupled to canisters 302 and 304, respectively. Check valves 142 and 144 are one way valves that are passively operated by the pressure differentials that occur as the canisters are pressurized and vented. Oxygen enriched gas, produced in canisters 302 and 304 pass from the canister into openings 542 and 544 of housing 410. A passage (not shown) links openings 542 and 544 to conduits 342 and 344, respectively. Oxygen enriched gas produced in canister 302 passes from the canister though opening 542 and into conduit 342 when the pressure in the canister is sufficient to open check valve 142. When check valve 142 is open, oxygen enriched gas flows through conduit 342 toward the end of housing 310. Similarly, oxygen enriched gas produced in canister 304 passes from the canister though opening 544 and into conduit 344 when the pressure in the canister is sufficient to open check valve 144. When check valve 144 is open, oxygen enriched gas flows through conduit 344 toward the end of housing 310.

Oxygen enriched gas from either canister, travels through conduit 342 or 344 and enters conduit 346 formed in housing 310. Conduit 346 includes openings that couple the conduit to conduit 342, conduit 344 and accumulator 106. Thus oxygen enriched gas, produced in canister 302 or 304, travels to conduit 346 and passes into accumulator 106.

After some time the gas separation adsorbent will become saturated with nitrogen and will be unable to separate significant amounts of nitrogen from incoming air. When the gas separation adsorbent in a canister reaches this saturation point, the inflow of compressed air is stopped and the canister is vented to remove nitrogen. Canister 302 is vented by closing inlet valve 122 and opening outlet valve 132. Outlet valve 132 releases the vented gas from canister 302 into the volume defined by the end of housing 310. Foam material may cover the end of housing 310 to reduce the sound made by release of gases from the canisters. Similarly, canister 304 is vented by closing inlet valve 124 and opening outlet valve 134. Outlet valve 134 releases the vented gas from canister 304 into the volume defined by the end of housing 310.

While canister 302 is being vented, canister 304 is pressurized to produce oxygen enriched gas in the same manner described above. Pressurization of canister 304 is achieved by closing outlet valve 134 and opening inlet valve 124. The oxygen enriched gas exits canister 304 through check valve 144.

Figure 7:
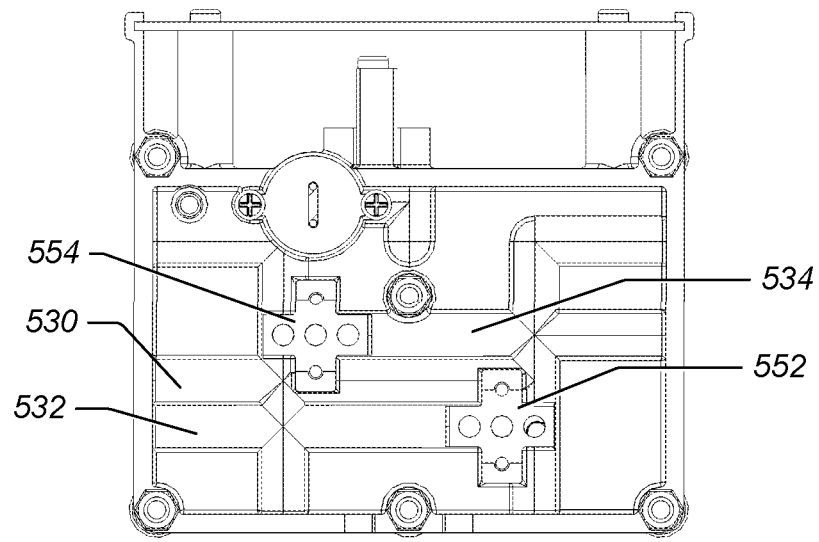
FIG. 7 depicts a perspective view of an embodiment of an opposing end of the canister system depicted in FIGS. 4 and 5.
Figure 8:
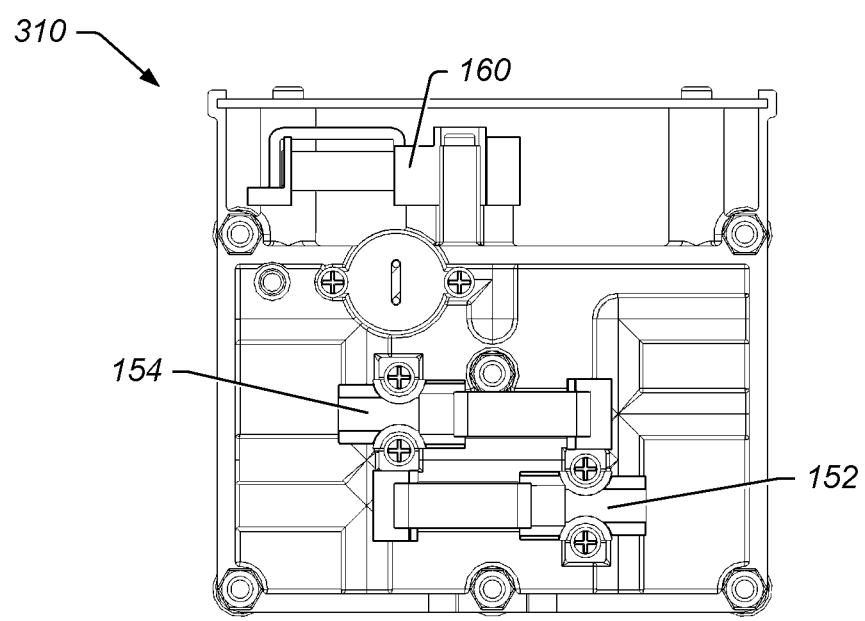
FIG. 8 depicts a perspective view of an embodiment of the assembled opposing end of the canister system end depicted in FIG. 7.

In an exemplary embodiment, a portion of the oxygen enriched gas may be transferred from canister 302 to canister 304 when canister 304 is being vented of nitrogen. Transfer of oxygen enriched gas from canister 302 to canister 304, during venting of canister 304, helps to further purge nitrogen (and other gases) from the canister. Flow of oxygen enriched gas between the canisters is controlled using flow restrictors and valves, as depicted in FIG. 1. Three conduits are formed in housing 510 for use in transferring oxygen enriched gas between canisters. As shown in FIG. 7, conduit 530 couples canister 302 to canister 304. Flow restrictor 151 (not shown) is disposed in conduit 530, between canister 302 and canister 304 to restrict flow of oxygen enriched gas during use. Conduit 532 also couples canister 302 to 304. Conduit 532 is coupled to valve seat 552 which receives valve 152, as shown in FIG. 8. Flow restrictor 153 (not shown) is disposed in conduit 532, between canister 302 and 304. Conduit 534 also couples canister 302 to 304. Conduit 534 is coupled to valve seat 554 which receives valve 154, as shown in FIG. 8. Flow restrictor 155 (not shown) is disposed in conduit 434, between canister 302 and 304. The pair of equalization/vent valves 152/154 work with flow restrictors 153 and 155 to optimize the air flow balance between the two canisters.

Oxygen enriched gas in accumulator 106 passes through supply valve 160 into expansion chamber 170 which is formed in housing 510. An opening (not shown) in housing 510 couples accumulator 106 to supply valve 160. In an embodiment, expansion chamber may include one or more devices capable of being used to determine an oxygen concentration of gas passing through the chamber.

Controller System

Operation of oxygen concentrator system 100 may be performed automatically using an internal controller 400 coupled to various components of the oxygen concentrator system, as described herein. Controller 400 includes one or more processors 410 and internal memory 420, as depicted in FIG. 1. Methods used to operate and monitor oxygen concentrator system 100 may be implemented by program instructions stored in memory 420 or a carrier medium coupled to controller 400, and executed by one or more processors 410. A non-transitory memory medium may include any of various types of memory devices or storage devices. The term "memory medium" is intended to include an installation medium, e.g., a Compact Disc Read Only Memory (CD-ROM), floppy disks, or tape device; a computer system memory or random access memory such as Dynamic Random Access Memory (DRAM), Double Data Rate Random Access Memory (DDR RAM), Static Random Access Memory (SRAM), Extended Data Out Random Access Memory (EDO RAM), Rambus Random Access Memory (RAM), etc.; or a non-volatile memory such as a magnetic media, e.g., a hard drive, or optical storage. The memory medium may comprise other types of memory as well, or combinations thereof. In addition, the memory medium may be located in a first computer in which the programs are executed, or may be located in a second different computer that connects to the first computer over a network, such as the Internet. In the latter instance, the second computer may provide program instructions to the first computer for execution. The term "memory medium" may include two or more memory mediums that may reside in different locations, e.g., in different computers that are connected over a network.

In some embodiments, controller 400 includes processor 410 that includes, for example, one or more field programmable gate arrays (FPGAs), microcontrollers, etc. included on a circuit board disposed in oxygen concentrator system 100. Processor 410 is capable of executing programming instructions stored in memory 420. In some embodiments, programming instructions may be built into processor 410 such that a memory external to the processor may not be separately accessed (i.e., the memory 420 may be internal to the processor 410).

Processor 410 may be coupled to various components of oxygen concentrator system 100, including, but not limited to compression system 200, one or more of the valves used to control fluid flow through the system (e.g., valves 122, 124, 132, 134, 152, 154, 160, or combinations thereof), oxygen sensor 165, pressure sensor 194, flow rate monitor 180, temperature sensors, fans, and any other component that may be electrically controlled. In some embodiments, a separate processor (and/or memory) may be coupled to one or more of the components.

Controller 400 is programmed to operate oxygen concentrator system 100 and is further programmed to monitor the oxygen concentrator system for malfunction states. For example, in one embodiment, controller 400 is programmed to trigger an alarm if the system is operating and no breathing is detected by the user for a predetermined amount of time. For example, if controller 400 does not detect a breath for a period of 75 seconds, an alarm LED may be lit and/or an audible alarm may be sounded. If the user has truly stopped breathing, for example, during a sleep apnea episode, the alarm may be sufficient to awaken the user, causing the user to resume breathing. The action of breathing may be sufficient for controller 400 to reset this alarm function. Alternatively, if the system is accidently left on when output conduit 192 is removed from the user, the alarm may serve as a reminder for the user to turn oxygen concentrator system 100 off.

Controller 400 is further coupled to oxygen sensor 165, and may be programmed for continuous or periodic monitoring of the oxygen concentration of the oxygen enriched gas passing through expansion chamber 170. A minimum oxygen concentration threshold may be programmed into controller 400, such that the controller lights an LED visual alarm and/or an audible alarm to warn the patient of the low concentration of oxygen.

Controller 400 is also coupled to internal power supply 180 and is capable of monitoring the level of charge of the internal power supply. A minimum voltage and/or current threshold may be programmed into controller 400, such that the controller lights an LED visual alarm and/or an audible alarm to warn the patient of low power condition. The alarms may be activated intermittently and at an increasing frequency as the battery approaches zero usable charge.

Further functions of controller 400 are described in detail in other sections of this disclosure.

A user may have a low breathing rate or depth if relatively inactive (e.g., asleep, sitting, etc.) as assessed by comparing the detected breathing rate or depth to a threshold. The user may have a high breathing rate or depth if relatively active (e.g., walking, exercising, etc.). An active/sleep mode may be assessed automatically and/or the user may manually indicate a respective active or sleep mode by a pressing button for active mode and another button for sleep mode. In some embodiments, a user may toggle a switch from active mode, normal mode, or sedentary mode. The adjustments made by the oxygen concentrator system in response to activating active mode or sleep mode are described in more detail herein.

Methods of Delivery of Oxygen Enriched Gas

The main use of an oxygen concentrator system is to provide supplemental oxygen to a user. Generally, the amount of supplemental oxygen to be provided is assessed by a physician. Typical prescribed amounts of supplemental oxygen may range from about 1 LPM to up to about 10 LPM. The most commonly prescribed amounts are 1 LPM, 2 LPM, 3 LPM, and 4 LPM. Generally, oxygen enriched gas is provided to the use during a breathing cycle to meet the prescription requirement of the user. As used herein the term "breathing cycle" refers to an inhalation followed by an exhalation of a person.

In order to minimize the amount of oxygen enriched gas that is needed to be produced to meet the prescribed amounts, controller 400 may be programmed to time delivery of the oxygen enriched gas with the user's inhalations. Releasing the oxygen enriched gas to the user as the user inhales may prevent unnecessary oxygen generation (further reducing power requirements) by not releasing oxygen, for example, when the user is exhaling. Reducing the amount of oxygen required may effectively reduce the amount of air compressing needed for oxygen concentrator 100 (and subsequently may reduce the power demand from the compressors).

Oxygen enriched gas, produced by oxygen concentrator system 100 is stored in an oxygen accumulator 106 and released to the user as the user inhales. The amount of oxygen enriched gas provided by the oxygen concentrator system is controlled, in part, by supply valve 160. In an embodiment, supply valve 160 is opened for a sufficient amount of time to provide the appropriate amount of oxygen enriched gas, as assessed by controller 400, to the user. In order to minimize the amount of oxygen required to meet the prescription requirements of a user, the oxygen enriched gas may be provided in a bolus when a user's inhalation is first detected. For example, the bolus of oxygen enriched gas may be provided in the first few milliseconds of a user's inhalation.

In an embodiment, pressure sensor 194 and/or flow rate sensor 185 may be used to determine the onset of inhalation by the user. For example, the user's inhalation may be detected by using pressure sensor 194. In use, a conduit for providing oxygen enriched gas is coupled to a user's nose and/or mouth (e.g., using a nasal cannula or a face mask). At the onset of an inhalation, the user begins to draw air into their body through the nose and/or mouth. As the air is drawn in, a negative pressure is generated at the end of the conduit, due, in part, to the venturi action of the air being drawn across the end of the delivery conduit. Pressure sensor 194 may be operable to create a signal when a drop in pressure is detected, to signal the onset of inhalation. Upon detection of the onset of inhalation, supply valve 160 is controlled to release a bolus of oxygen enriched gas from the accumulator 106.

In some embodiments, pressure sensor 194 may provide a signal that is proportional to the amount of positive or negative pressure applied to a sensing surface. The amount of the pressure change detected by pressure sensor 194 may be used to refine the amount of oxygen enriched gas being provided to the user. For example, if a large negative pressure change is detected by pressure sensor 194, the volume of oxygen enriched gas provided to the user may be increased to take into account the increased volume of gas being inhaled by the user. If a smaller negative pressure is detected, the volume of oxygen enriched gas provided to the user may be decreased to take into account the decreased volume of gas being inhaled by the user. A positive change in the pressure indicates an exhalation by the user and is generally a time that release of oxygen enriched gas is discontinued. Generally while a positive pressure change is sensed, valve 160 remains closed until the next onset of inhalation.

In some embodiments, the sensitivity of the pressure sensor 194 may be affected by the physical distance of the pressure sensor 194 from the user, especially if the pressure sensor is located in oxygen concentrator system 100 and the pressure difference is detected through the tubing coupling the oxygen concentrator system to the user. In some embodiments, the pressure sensor may be placed in the airway delivery device used to provide the oxygen enriched gas to the user. A signal from the pressure sensor may be provided to controller 400 in the oxygen concentrator 100 electronically via a wire or through telemetry such as through BLUETOOTH® (Bluetooth, SIG, Inc. Kirkland, Wash.) or other wireless technology.

In an embodiment, the user's inhalation may be detected by using flow rate sensor 185. In use, a conduit for providing oxygen enriched gas is coupled to a user's nose and/or mouth (e.g., using a nasal cannula or face mask). At the onset of an inhalation, the user begins to draw air into their body through the nose and/or mouth. As the air is drawn in, an increase in flow of gas passing through conduit is created. Flow rate sensor 185 may be operable to create a signal when an increase in flow rate is detected, to signal the onset of inhalation. Upon detection of the onset of inhalation, supply valve 160 is controlled to release a bolus of oxygen enriched gas from the accumulator 106.

A user breathing at a rate of 30 breaths per minute (BPM) during an active state (e.g., walking, exercising, etc.) may consume two and one-half times as much oxygen as a user who is breathing at 12 BPM during a sedentary state (e.g., asleep, sitting, etc.). Pressure sensor 194 and/or flow rate sensor 185 may be used to determine the breathing rate of the user. Controller 400 may process information received from pressure sensor 194 and/or flow rate sensor 185 and determine a breathing rate based on the frequency of the onset of inhalation. The detected breathing rate of the user may be used to adjust the bolus of oxygen enriched gas. The volume of the bolus of oxygen enriched gas may be increased as the users breathing rate increase, and may be decreased as the users breathing rate decreases. Controller 400 may automatically adjust the bolus based on the detected activity state of the user. Alternatively, the user may manually indicate a respective active or sedentary mode by selecting the appropriate option on the control panel of the oxygen concentrator. Alternatively, a user may operate controller 400 from a remote electronic device. For example, a user may operate the controller using a smart phone or tablet device.

In some embodiments, if the user's current activity level as assessed using the detected user's breathing rate exceeds a predetermined threshold, controller 400 may implement an alarm (e.g., visual and/or audio) to warn the user that the current breathing rate is exceeding the delivery capacity of the oxygen concentrator system. For example, the threshold may be set at 20 breaths per minute.

Methods of determining the breathing rate of a user typically count the number of breathes taken by the user over a pre-determined time and calculate the breathing rate. When determining the breathing rate of a user, all breaths measured during the pre-determined time period are typically used to calculate the breathing rate. Such a method, however, can lead to significant errors due to sudden changes in the breathing rate of the user. For example, while sleeping it is know that the times between breaths may vary greatly for an individual. Breathing patterns normally change during sleep. During deep sleep, breathing slows and becomes lighter as the body rests. During light sleep and REM, breathing can resemble breathing patterns of the person when awake. Periods of heavy breathing may also occur during dreams. Changes in breathing rate can occur quickly while a user is sleeping and even during awake periods. If the delivery of oxygen enriched gas is not adapted to the breathing patterns of the user properly, oxygen enriched gas may be wasted, by providing the oxygen enriched gas for too long, or may be insufficient, if the oxygen enriched gas is provided for too short a period.

Attempts have been made to take into account the erratic breathing of a user. For example, U.S. Pat. No. 7,841,343 to Deane et al. ("Deane") described the use of a blind time to help compensate for erratic breathing. Specifically, Deane teaches that after a bolus of oxygen enriched gas is delivered to a user, a controller enters a blind time. During this blind time the controller will not accept any triggers to deliver oxygen enriched gas. This time may range from 0.5 to 3 seconds after the bolus is delivered. After this blind time has elapsed the controller sets the inspiration breath pressure threshold to a low level and gradually increases the sensitivity until a breath is detected. According to Deane, this helps to vary the bolus delivery in response to changes in the users breathing.

The method of Deane relies on a blind time in which no breaths are detected. Thus, if the user starts breathing rapidly, shortly after the delivery of a bolus of oxygen enriched gas, the method of Deane may be delayed in reacting to the change in breathing. In the worst case scenario, the user may change to a breathing rate in which every other breath falls within the blind time, leading to the false indication that the user is breathing at a breathing rate that is half the actual breathing rate. Such a situation can lead to oxygen depravity in the individual due to an insufficient amount of oxygen being supplied to the user.

Applicant has devised an improved method of determining a breathing rate, and controlling the inspiration breath pressure threshold based on the determined breathings. In an embodiment, the controller determines the breathing rate based on measuring a predetermined number of breaths (at least three) and discarding information related to the last breath measured. In this method the time between the penultimate breath and the last breath is not used to determine the average breathing rate. The breathing rate, determined using the information collected from the remaining breaths, was found to give a more accurate indication of the current breathing rate of the user. Such a method also provides a way to take into account erratic breathing patterns without having to resort to the extreme measure of creating artificial "blind times," as discussed in Deane.

Over a period of time, controller 400 may collect and store the number of breaths. Based on the number of breaths, or the average time between breaths, over the period of time a breathing rate may be calculated. In some embodiments, the period of time is divided into equal time units. The number of breaths, or the average time between breaths, is determined in each time unit for the set period of time. The number of breaths, or average time between breaths, per time unit is used to determine a breathing rate. In some embodiments, the breathing rate in the last time unit is not used to determine if the delivery parameters should be changed. For example, if a period of time is broken up into 5 equal time units, the breathing rate determined for the last time unit is not used to determine an average breathing rate (for example, average breaths per minute).

For example, controller 400 may collect the number of breaths over a 5 minute period of time. During the 5 minutes, a user may have a breathing rate of 15 breaths per minute ("BPM") for the first minute of the 5 minute time period, 10 BPM during the second minute of the 5 minute time period, 25 BPM during the third minute of the 5 minute time period, 30 BPM during the fourth minute of the 5 minute time period, and 40 BPM during the fifth minute of the 5 minute time period. The 40 BPM may be ignored and the remaining breaths averaged (for example, to determine an average breathing rate of 20 BPM. The breathing rate determined during the last minute of the 5 minute time period may be used for averaging of the next 5 minute time period. For example the last minute of the 5 minute time period may be used as the first minute of the next five minute time period. Alternatively, the five minute time period analyzed may be shifted by a minute. In this case, the second minute of the five minute period just analyzed becomes the first minute of the next five minute period. The fifth minute (ignored in the first breathing rate analysis), becomes the fourth minute of the next breathing rate analysis. In either case the last minute is ignored in the breathing rate analysis.

In another embodiment, the breathing rate may be determined by monitoring the time between each breath for at least three breaths. In some embodiments, the times between each of four, five, six, seven, eight, nine, ten, fifteen, sixteen, seventeen, or twenty successive breaths are measured and used to determine an average breathing rate. In this method the time between the penultimate breath and the last breath is ignored, with the breathing rate based on the time between the breaths up to the penultimate breath. For example, if 5 successive breaths are used to determine a breathing rate, the time between the $4^{th}$ and $5^{th}$ breath is discarded when determining the breathing rate. For example if the following times between breaths are obtained: $1^{st}$-$2^{nd}$: 4.5 sec., $2^{nd}$-$3^{rd}$: 4.7 sec, $3^{rd}$-$4^{th}$ 4.2 sec, $4^{th}$-$5^{th}$: 5.2 sec, the average time between breaths is determined by averaging the first three times (4.5 sec, 4.7 sec, and 4.2 sec) and ignoring the last breath (5.2 sec). In this manner the average time between breaths is 4.47, giving an average breathing rate of 13.4 breathes per minute.

Using the average breathing rate, the inspiration breath pressure threshold may be adjusted relative to the current inspiration breath pressure threshold. Controller 400 may determine that the average breathing rate has changed from less than 15 breaths per minute to greater than 15 breaths per minute. Controller 400 may send an electronic signal to pressure sensor 194 that raises the threshold breath pressure inspiration relative to the current inspiration breath pressure threshold. When the determined average breathing rate changes from greater than 10 breaths per minute to less than 10 breaths per minute, controller 400 may send an electronic signal to the pressure sensor 194 that lowers the inspiration breath pressure threshold relative to the current inspiration breath pressure threshold. Controller 400 may determine that the average breathing rate is between 10 breaths per minute and 15 breaths per minute, and determine that no change in the current inspiration breath pressure threshold is necessary. If the average breathing rate is less than 5 breaths per minute then controller 400 may trigger an alarm. If the inspiration breath pressure threshold has been lowered relative to the current inspiration breath pressure threshold and no inspiration breath pressure is detected after a period of time (for example, 75 seconds), then controller 400 may trigger an alarm.

In another embodiment, the change in the inspiration breath pressure threshold may be adjusted by looking at the change in breathing rate over a predetermined period of time. For example, a change in breathing rate can be monitored by creating successive groupings of three or more breaths. For each successive grouping of three or more breaths, the breathing rate is determined (e.g., by calculating the breathing rate based on an average time between each breath in the grouping). The breathing rate from each grouping is compared to the next grouping to determine how the breathing rate is changing. If the breathing rate is increasing over three or more successive groupings (e.g., the breathing rate increases in at least two of the groupings), the controller may increase the inspiration breath pressure threshold. If the breathing rate is decreasing over three or more successive groupings (e.g., the breathing rate decreases in at least two of the groupings), the controller may lower the inspiration breath pressure threshold.

In a specific example, the time between each of seventeen successive breaths is measured. The breaths are then divided into four groupings, with each grouping having the inhalation times for four successive breaths. The groupings would then look as shown below, the number in parenthesis refers to the time between the breaths:

1 (5.8 s) 2 (5.0 s) 3 (4.2 s) 4 BPM=12
(4.0 s) 5 (3.5 s) 6 (3.5 s) 7 (3.0 s) 8 BPM=17
(3.0 s) 9 (3.4 s) 10 (3.6 s) 11 (3.5 s) 12 BPM=18
(2.6 s) 13 (2.6 s) 14 (2.4 s) 15 (2.0 s) 16 BPM=25
(2.7 s) 17

The last time (the time between breath 16 and 17, is not used to determine the breathing rate. In the above example, the first grouping (breaths 1-4) exhibits a breathing rate of 12 BPM. The second grouping exhibits a breathing rate of 17 BPM, which shows that the subjects breathing rate is increasing. Instead of changing the inspiration breath pressure threshold, the controller goes into a "watch" mode. In the "watch" mode the controller is alerted that a change in the inspiration breath pressure threshold may be needed. The controller then looks at the third grouping. The third grouping exhibits a breathing rate of 18 BPM. A breathing rate that is within +/−2 of the previous breathing rate, is not considered to have changed. Since the breathing rate has not changed (as defined above) from the second grouping to the third grouping, the controller remains in watch mode. The controller then looks at the change between the third and fourth groupings. The fourth grouping exhibits a breathing rate of 25 BPM. Since the controller has now seen a second increase among the four groupings measured, the controller increase the inspiration breath pressure threshold. The controller will continue to take additional groupings (in this example, of four successive breaths, excluding the last breath taken) and continue to evaluate whether the inspiration breath pressure threshold should be adjusted.

In some embodiments, rather than ignoring the last breath, the last grouping is ignored. For example, in the above example, the controller bases the decision to change the inspiration breath pressure threshold based on the first three groupings, ignoring the last ($4^{th}$) grouping. Under these circumstances, the inspiration breath pressure threshold is not changed until additional groupings are taken and it is determined if the increase in breathing rate is continued.

In alternate embodiments, the controller may base decisions on the actual BPM rather than the change in BPM. For example, if the BPM changes to less than 10 breaths per minute in a grouping, the controller may go into a watch mode. If the BPM remains below 10 BPM in one of the next two groupings, the controller may send an electronic signal to the pressure sensor that lowers the inspiration breath pressure threshold relative to the current inspiration breath pressure threshold. If the BPM is between 10 breaths per minute and 15 breaths per minute, then no change is made to the inspiration breath pressure threshold. If the BPM changes to more than 15 breaths per minute in a grouping, the controller may go into a watch mode. If the BPM remains above 15 BPM in one of the next two groupings, the controller may send an electronic signal to the pressure sensor that increase the inspiration breath pressure threshold relative to the current inspiration breath pressure threshold. In this embodiment, as discussed above, the last breath detected or the last grouping measured may be ignored when determining if the inspiration breath pressure threshold should be changed.

Figure 10:
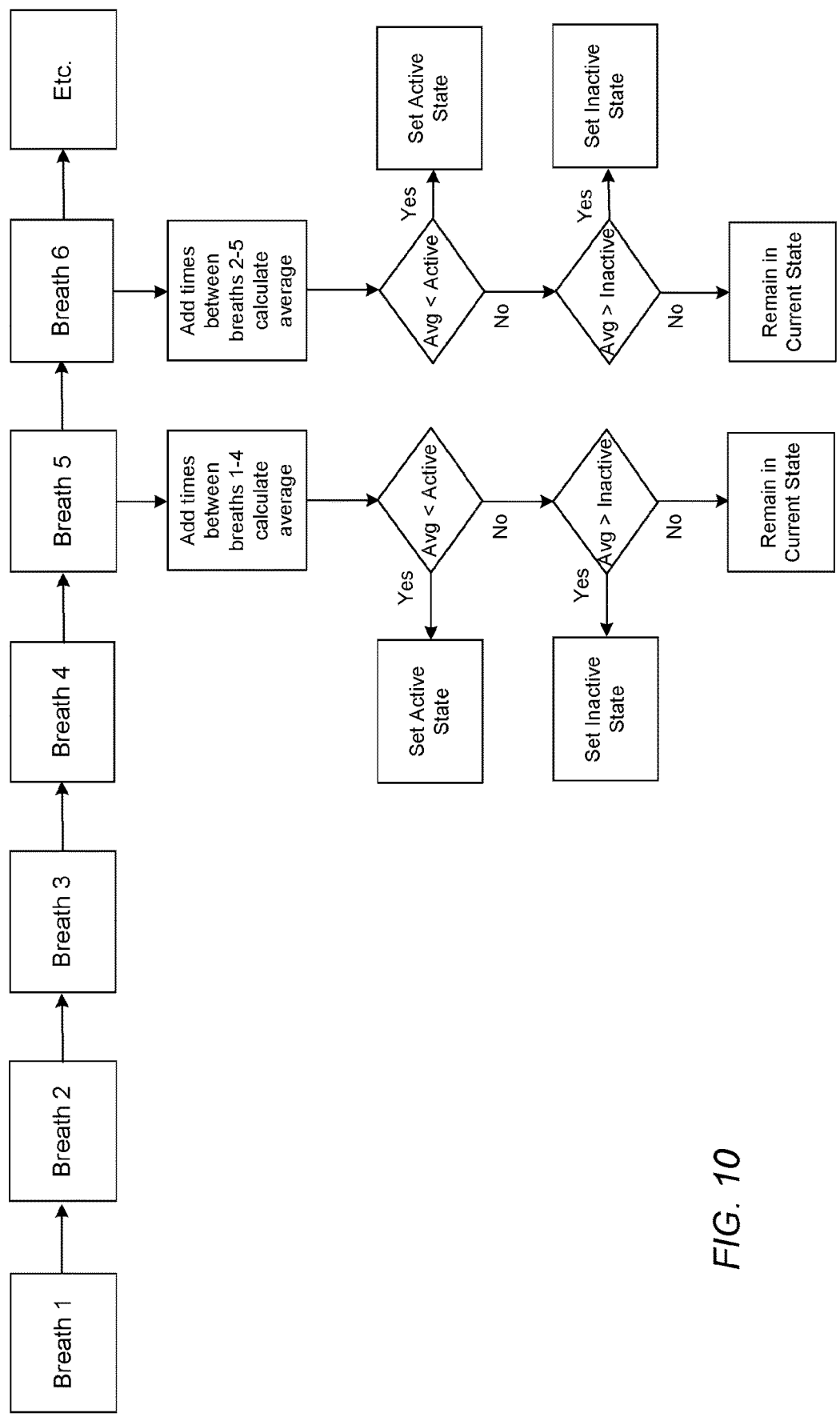
FIG. 10 depicts a flowchart of a process for adjusting the inspiration breath pressure threshold.

In some embodiments, it is not necessary to calculate the breathing rate, but instead the time between breaths may be used in a decision making process. A flow chart of a process of adjusting the inspiration breath pressure threshold is shown in FIG. 10. During use, the times between at least three consecutives breaths is measured. When the time between, for example, the fourth breath and the fifth breath is measured, the controller determines if a change in the inspiration breath pressure threshold is needed. The times between breaths 1 and 2; 2 and 3; and 3 and 4 are used to determine the average time between breaths. The time between breath 4 and breath 5 is not used to determine the average time between breaths. The average time between breaths 1-4 is then compared to predetermined values. In one embodiment, the subject is considered to be in an active state if the average time between breaths is less than 4 seconds. It should be understood that other times can be used. Thus process therefore includes comparing the average time between breaths of the subject to the predetermined active state time. If the average time between breaths of the subject is less than the active state time, the controller sets the inspiration breath pressure threshold to a high pressure.

If the average time between breaths of the subject is greater than the active state time, the controller compares the time to an inactive state time. In one embodiment, the subject is considered to be in an inactive state if the average time between breaths is greater than 6 seconds. It should be understood that other times can be used. If the average time between breaths of the subject is greater than 6 seconds, the controller sets the inspiration breath pressure threshold to a low pressure. If the average time between breaths of the subject is between 4 and 6 seconds, the controller does not change the inspiration breath pressure threshold.

As shown in FIG. 10, when the breath 6 is taken, the process is repeated, however, the average is now based on the times between breath 2 and breath 5. Once the average time between breaths 2-5 is determined, the same process as discussed above is used to determine whether the inspiration breath pressure threshold should be changed, and, if it should be changed, whether it should be set to a high pressure (active) or a low pressure (inactive). This process may be continued as long as oxygen is being provided to the user.

In some embodiments, controller 400 may send a signal to adjust pressure sensor 194 to adjust the threshold inspiration breath pressure based on the ratio of the change in absolute pressure with respect to time monitored over at least three breaths. In some embodiments, the change in absolute pressure with respect to time between each of four, five, six, seven, eight, nine, ten, fifteen or twenty successive breaths are measured and used to determine a ratio of change in absolute pressure with respect to time. Controller 400 may determine a ratio of the change in absolute pressure with respect to time based during a breathing period and store the information in a non-transitory medium. Based on the determined ratio between the change in absolute pressure with respect to time, controller 400 may send an electronic signal to breath pressure sensor 194 that adjusts the inspiration breath pressure threshold. If ratio is assessed to be negative, and less than, or equal to, −0.5 controller 400 may send an electronic signal to breath pressure sensor 194 that lowers the inspiration breath pressure threshold relative to the current inspiration breath pressure threshold. For example, if the ratio is assessed to be about −1.5 to about −0.5, (i.e., less than or equal to −0.5), controller 400 may send an electronic signal to breath pressure sensor 194 that lowers the inspiration breath pressure threshold relative to the current inspiration breath pressure threshold. If the ratio is assessed to be slightly positive or slightly negative (e.g., between −0.5 to +0.5), controller 400 may send an electronic signal to breath pressure sensor 194 that keeps the inspiration breath pressure threshold the same as the current inspiration breath pressure threshold. If the ratio is positive, and, for example, greater than or equal to +0.5, for example, controller 400 may send an electronic signal to breath pressure sensor 194 that raises the inspiration breath pressure threshold relative to the current inspiration breath pressure threshold.

In some embodiments, controller 400 may operate the oxygen concentrator based on the change in the inspiration breath pressure threshold. The frequency and/or duration of the provided oxygen enriched gas to the user relative to the current frequency and/or duration may be adjusted based on the change in the inspiration breath pressure threshold. Upon determining that the inspiration breath pressure threshold has been lowered, the controller 400 may switch the oxygen concentrator to a sedentary mode. Controller 400 may switch the oxygen concentrator to an active mode, when the inspiration breath pressure threshold has been raised.

Figure 9:
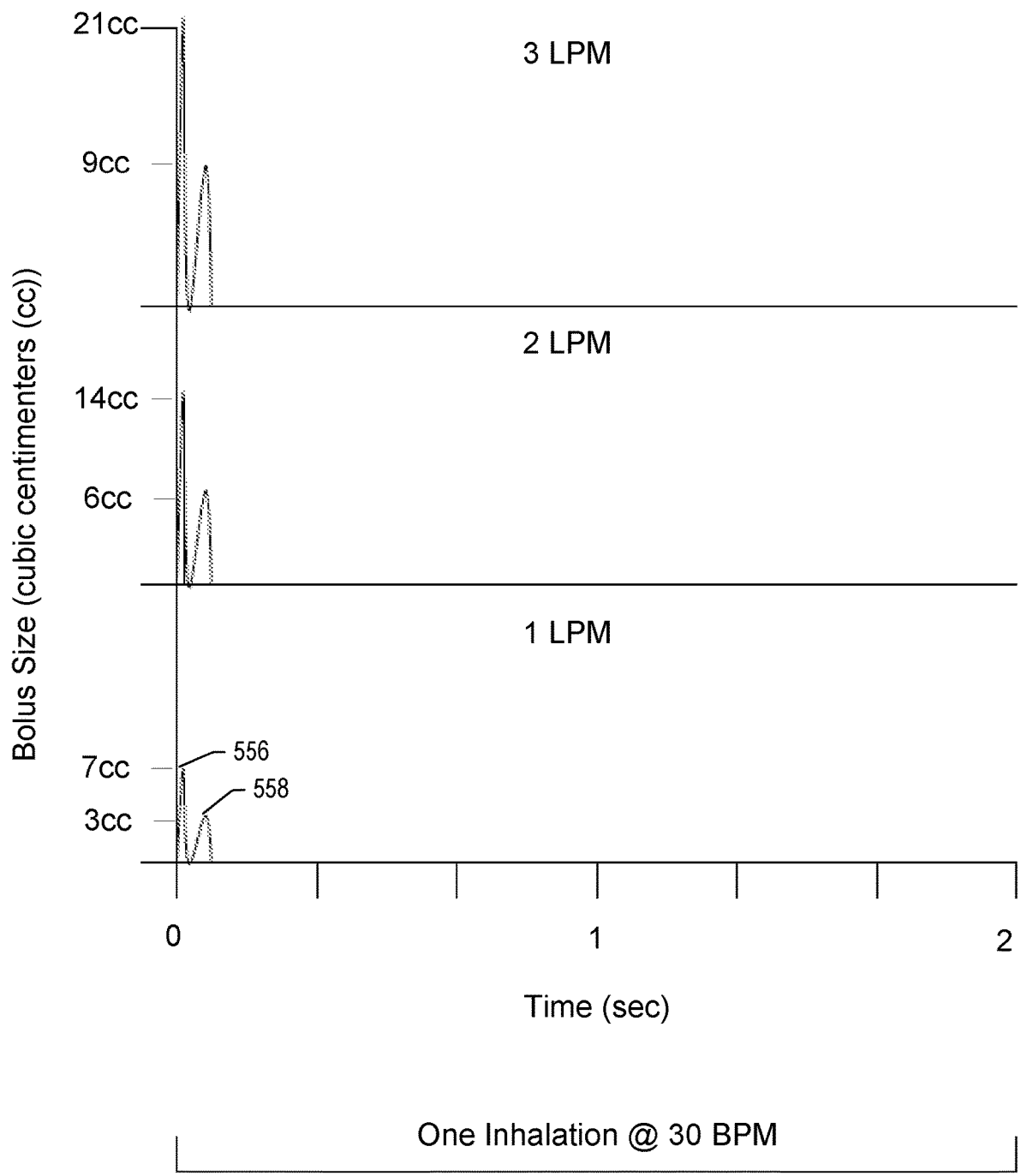
FIG. 9 depicts various profiles of embodiments for providing oxygen enriched gas from an oxygen concentrator.

In some embodiments, as seen in FIG. 9, the bolus of provided oxygen enriched gas may include two or more pulses. For example, with a one liter per minute (LPM) delivery rate, the bolus may include two pulses: a first pulse 556 at approximately 7 cubic centimeters and a second pulse 558 at approximately 3 cubic centimeters. Other delivery rates, pulse sizes, and number of pulses are also contemplated. For example, at 2 LPMs, the first pulse may be approximately 14 cubic centimeters and a second pulse may be approximately 6 cubic centimeters and at 3 LPMs, the first pulse may be approximately 21 cubic centimeters and a second pulse may be approximately 9 cubic centimeters. In some embodiments, the larger pulse 556 may be provided when the onset of inhalation is detected (e.g., detected by pressure sensor 194). In some embodiments, the pulses may be provided when the onset of inhalation is detected and/or may be spread time-wise evenly through the breath. In some embodiments, the pulses may be stair-stepped through the duration of the breath. In some embodiments, the pulses may be distributed in a different pattern. Additional pulses may also be used (e.g., 3, 4, 5, etc. pulses per breath). While the first pulse 556 is shown to be approximately twice the second pulse 558, in some embodiments, the second pulse 558 may be larger than the first pulse 556. In some embodiments, pulse size and length may be controlled by, for example, supply valve 160 which may open and close in a timed sequence to provide the pulses. A bolus with multiple pulses may have a smaller impact on a user than a bolus with a single pulse. The multiple pulses may also result in less drying of a user's nasal passages and less blood oxygen desaturation. The multiple pulses may also result in less oxygen waste.

In some embodiments, the sensitivity of the oxygen concentrator 100 may be selectively attenuated to reduce false inhalation detections due to movement of air from a different source (e.g., movement of ambient air). For example, the oxygen concentrator 100 may have two selectable modes—an active mode and an inactive mode. In some embodiments, the user may manually select a mode (e.g., through a switch or user interface). In some embodiments, the mode may be automatically selected by the oxygen concentrator 100 based on a detected breathing rate. For example, the oxygen concentrator 100 may use the pressure sensor 194 to detect a breathing rate of the user. If the breathing rate is above a threshold, the oxygen concentrator 100 may operate in an active mode (otherwise, the oxygen concentrator may operate in an inactive mode). Other modes and thresholds are also contemplated.

In some embodiments, in active mode, the sensitivity of the pressure sensor 194 may be mechanically, electronically, or programmatically attenuated. For example, during active mode, controller 400 may look for a greater pressure difference to indicate the start of a user breath (e.g., an elevated threshold may be compared to the detected pressure difference to determine if the bolus of oxygen should be released). In some embodiments, the pressure sensor 194 may be mechanically altered to be less sensitive to pressure differences. In some embodiments, an electronic signal from the pressure sensor may be electronically altered to ignore small pressure differences. This can be useful when in active mode. In some embodiments, during the inactive mode the sensitivity of the pressure sensor may be increased. For example, the controller 400 may look for a smaller pressure difference to indicate the start of a user breath (e.g., a smaller threshold may be compared to the detected pressure difference to determine if the bolus of oxygen should be released). In some embodiments, with increased sensitivity, the response time for providing the bolus of oxygen during the user's inhalation may be reduced. The increased sensitivity and smaller response time may reduce the size of the bolus necessary for a given flow rate equivalence. The reduced bolus size may also reduce the size and power consumption of the oxygen concentrator 100.

Providing a Bolus Based on Inhalation Profile

In an embodiment, the bolus profile can be designed to match the profile of a particular user. To do so, an inhalation profile may be generated based on information gathered from pressure sensor 194 and flow rate sensor 185. An inhalation profile is assessed based on, one or more of the following parameters: the breathing rate of the user; the inhalation volume of the user; the exhalation volume of the user; the inhalation flow rate of the user; and the exhalation flow rate of the user. The breathing rate of the user may be assessed by detecting the onset of inhalation using pressure sensor 194 or flow rate sensor 185 as previously discussed. Inhalation volume may be assessed by measuring the change in pressure during inhalation and calculating or empirically assessing the inhalation volume based on the change in pressure. Alternatively, inhalation volume may be assessed by measuring the flow rate during inhalation and calculating or empirically assessing the inhalation volume based on the flow rate and the length of the inhalation. Exhalation volume may be assessed in a similar manner using either positive pressure changes during exhalation, or flow rate and exhalation time. Inhalation flow rate of the user is measured from shortly after the onset of inhalation. Detection of the end of inhalation may be from the pressure sensor or the flow rate sensor. When onset of inhalation is detected by the pressure sensor, the onset is characterized by a drop in pressure. When the pressure begins to increase, the inhalation is considered complete. When onset of inhalation is detected by the flow rate sensor, the onset is characterized by an increase in the flow rate. When the flow rate begins to decrease, the inhalation is considered complete.

There is a minimum amount of oxygen necessary for a person to remain conscious. A person who is breathing rapidly is bringing in a lower volume of air in each breath, and thus, requires less oxygen enriched gas per inhalation. While there is some variation from patient to patient, this relationship can be used to establish the mean flow rate for each breath mathematically. By measuring a large population of patients, the profile of the relative flow from onset of inhalation to the onset of exhalation may be established. Using this flow profile as a template, the calculated actual flow based on breathing rate can be adjusted mathematically to a calculated actual flow profile. This profile can be used to adjust the opening and closing of the delivery valve to create an idealized profile for the patient based on their breathing rate. Inhalation profile data gathered from a population of users may be used to create an algorithm that makes the appropriate adjustments based on the detected inhalation profile. Alternatively, a look up table may be used to control valve actuation durations and pulse quantities based on a detected inhalation profile.

Measuring the inhalation profile of the patient provides a more accurate basis for control of the bolus of oxygen enriched gas being provided to the patient. For example, basing the delivery of oxygen enriched gas on the onset of inhalation may not take into account differences between individual users. For example, people having a similar breathing rate can have different inhalation/exhalation volume, inhalation/exhalation flow rates and, thus, different bolus requirements necessary to produce the prescribed amount of oxygen. In one embodiment, an inhalation profile is created based on the flow rate of air during inhalation and the duration of inhalation. The inhalation profile can then be used as a predictor of the volume of air taken in by a specific user during inhalation. Thus, inhalation profile information can be used to modify the amount of oxygen enriched air provided to the user to ensure that the prescribed level of oxygen is received. The amount of oxygen provided to a user may be adjusted by modifying the frequency and or duration of release of oxygen enriched gas from the accumulator with supply valve 160. By tracking the inhalation profile of the patient controller adjusts the delivery supply valve actuation to idealize the bolus profile to provide the oxygen at the maximum rate without causing wasteful retrograde flow.

Automatic Delivery of Oxygen Enriched Gas Based on Average Breathing Rate

It is important for patients to continually receive the necessary oxygen treatment. In some cases, however, the detection of breath can become difficult. Some patients, especially when resting or sleeping, may switch from nose breathing to mouth breathing, making it difficult to determine when a breath is being taken if the pressure sensor is in the nasal cannula. It has been found, however, that even if the patient has switched from nose breathing to mouth breathing, it can still be beneficial to deliver oxygen to the nasal region of the patient. Having an increased concentration of oxygen in the nasal region of the patient allows some oxygen to be taken in by the patient through the nose, since mouth breathing typically does not totally exclude some air from entering the nasal passages. It is therefore important to have an algorithm for having the oxygen concentrator deliver oxygen to the patient, even when no breathing is detected. Such an algorithm, however, needs to be designed to conserve the oxygen enriched gas produced by the oxygen concentrator by not delivering oxygen when no necessary.

In an embodiment, the automatic delivery of oxygen enriched gas from an oxygen concentrator is based on an average breathing rate of the patient, measured as either breath per minute ("bpm") or time between breaths. In an embodiment, the time between a plurality of successive breaths is measured. A breath is determined to begin when a drop in pressure is measured using a pressure sensor coupled to an outlet of a conduit coupling the user to an oxygen enriched gas source. The average time between each of the successive breaths is determined or the average bpm is determined. The time between the penultimate breath and the last breath, however, is not used to determine the average time, for the same reasons discussed previously in the application.

An inspiration breath pressure threshold for the pressure sensor is set based on the determined average time. The breath pressure threshold is set to an active mode breath pressure threshold if the average time is less than a predefined time. The breath pressure threshold is set to a sleep mode breath pressure threshold if the average time is greater than a predefined time. In some embodiments, the predefined time is a time between about 6 sec. and about 12 sec., with 8 sec. being the preferred time for most patients. The sleep mode breath pressure threshold is lower than the active mode breath pressure threshold so that the pressure sensor is more likely to pick up breaths taken by the patient in sleep mode.

Sleep mode can be also be entered be measuring the time since the penultimate breath. In such an embodiment, two timers are used, an even timer and an odd timer. When an odd breath is taken (breath $1^{st}$, $3^{rd}$, $5^{th}$, etc.) then the odd time is reset to a time equal to the maximum time expected for two breaths to be taken. In some embodiments, the maximum time for two breaths to be taken is set in the range from about 25 sec. to about 35 sec., with 30 sec. being preferred. In other embodiments, the maximum time for two breaths is continually determined as two times the average time determined from the patient's breathing pattern. When an even breath is taken ($2^{nd}$, $4^{th}$, $6^{th}$, etc.), the even timer is set to a time equal to the maximum time expected for two breaths. If either timer reaches the maximum time, the breath pressure threshold is set to a sleep mode breath pressure threshold. Setting to a sleep mode breath pressure threshold will improve the chances of detecting a breath in the case that the patient has changed from active activity to reduced activity.

Once in sleep mode, the times are continually monitored and compared to the determined average time determined between breaths. In an embodiment, the time elapsed according to the odd timer and the time elapsed according to the even timer are added together and compared to a function of the determined average breathing time. In one embodiment, if the sum of the elapsed times is greater than a constant times the determined average breathing time, then the oxygen concentrator will automatically provide oxygen enriched gas to the user. In some embodiments, the constant is between about 1.5 and 2.5, with a constant of 2.0 being preferred.

During automatic delivery of oxygen enriched gas, the oxygen enriched gas is delivered every 3-4 seconds until breaths are once again detected. During automatic delivery of oxygen enriched gas, the time between each automatic delivery of a bolus of oxygen is varied randomly between 3-4 seconds. Alternately, the time is varied by a constant amount cycling between 3-4 seconds. For example, the time between each delivery of oxygen enriched gas may begin at 3 seconds, then after one or more breaths are delivered the delay time for each breath may be changed to 3.1, then 3.2, etc. until a delay time of 4 seconds is reached. Once the 4 second mark is reached, the time may be reduced in the same manner (4.0, then 3.9, then 3.8, etc.) until the 3 second mark is reached. This pattern may be continued until detectable breathing is resumed by the patient.

The above method may be implemented by a processor operably coupled to the pressure sensor. The processor executes non-transitory program instructions which allow the processor to implement the method. In an embodiment, the method is implemented using three timers. Timer_1 measures the time since an odd numbered breath. Timer_2 measures the time since an even numbered breath. Timer_3 measures the time between each breath and is reset when a breath is detected or a false breath is registered. The method relies on a sampling routine which continually monitors the timers and adjusts the parameters based on the timers and the average breath times.

When the oxygen concentrator apparatus is turned on, the system is initialized. The initialization routine is set forth below:

Initialize System

Timer_1=MAX_BREATH_TIME

Timer_2=TWO_BREATH_TIME

Breath_Index=0

Breath_Register[1 . . . 5]=8 sec

Average_Breath_Rate=[SUM (Breath_Register [2 . . . 5])]/4

Timer_1 is the odd timer;

MAX_BREATH_TIME is a constant that is set at the maximum time allowed between breaths (e.g. 15 sec.);

Timer_2 is the even timer

TWO_BREATH_TIME is a constant that is set at the maximum time allowed for two breaths (e.g. 30 sec.);

Breath_Index is a variable used to count the number of breaths

Breath_Register[1 . . . 5] is an array of 5 memory locations used to store the time between 6 successive breaths. Breath_Register[5] stores the time elapsed between the $1^{st}$ breath taken in a series of 6 successive breaths to the $2^{nd}$ breath taken in the series. Breath_Register[4] stores the time elapsed from the $2^{nd}$ breath to the $3^{rd}$ breath. Breath_Register[3] stores the time elapsed from the $3^{rd}$ breath to the $4^{th}$ breath. Breath_Register[2] stores the time elapsed from the $4^{th}$ breath to the $5^{th}$ breath. Breath_Register[1] stores the time elapsed from the $5^{th}$ breath (the penultimate breath) to the $6^{th}$ breath (the last breath detected).

Average_Breath_Rate is determined by calculating the average of the times in Breath_Registers [2-5]. Breath_Register [1] is not used to calculate the average breath time (or rate).

After initialization, the Sampling Routine continually monitors the pressure sensor for the detection of a breath. The Sampling Routine also continually monitors the Timer_1 and Timer_2 looking for the timer to time out. The current implementation sets each timer to the maximum time allowed and runs the timer backward toward zero. In such an implementation, when a timer reaches zero, the timer is considered to have "timed out." It should be understood, however that the timers can also be implemented in a forward direction with minimal changes to the programming. The Sampling Routine is set forth below:

Sampling Routine (every 1 msec)

Average_Breath_Rate>SLEEP_BREATH_TIME, Y— Go to Sleep Mode; N—Go to Active Mode

Breath Detected=Y—Go to Active Breath Detection Routine or Sleep Breath Detection Routine Timer_1==0; Y—Go to Active No Breath Detection Routine or Sleep No Breath Detection Routine Timer_2==0; Y—Go to Active No Breath Detection Routine or Sleep No Breath Detection Routine SLEEP_BREATH_TIME is a constant that is set between at a time between about 8 sec. and about 12 sec.

Based on the results of the Sampling Routine, the appropriate action routine is accessed. The action routines include: Active Breath Detection Routine; Sleep Breath Detection Routine; Active No Breath Detection Routine; and Sleep No Breath Detection Routine. Each of these routines are set forth below:

Active Mode Breath Detection Routine
Shift Breath-Registers—Add new time to Breath_Register[1]
Breath_Index=Breath_Index+1
If Breath_Index is odd; Breath_Register[1]=(MAX_BREATH_TIME−Timer_2)
If Breath_Index is even; Breath_Register[1]=(MAX_BREATH_TIME−Timer_1)
Average_Breath_Rate=[SUM (Breath_Register [2 . . . 5])]/4
If Average_Breath_Rate>SLEEP_BREATH_TIME (10 sec) GOTO SLEEP MODE
If index is odd; Timer_1=TWO_BREATH_TIME;
If index is even; Timer_2=TWO_BREATH_TIME;

The Active Mode Breath Detection Routine is activated if a new breath is detected while the device is in active mode. This routine starts by shifting the Breath_Registers. This is done by overwriting each register with the value from the adjacent register. Thus, Breath_Register[5] is overwritten with the value from Breath_Register[4]; Breath_Register[4] is then overwritten by the value from Breath_register[3], etc. The time from the last breath to the newly detected breath is placed in Breath_Register[1]. After the breaths are shifted, a new Average_Breath_Rate is determined. The new Average_Breath_Rate is then compared to the constant, SLEEP_BREATH_TIME. If Average_Breath_Rate (stored as an average time elapsed per breath) is greater than SLEEP_BREATH_TIME, the system will go into Sleep Mode by lowering the inspiration breath pressure threshold for the pressure sensor. Timer_1 or Timer_2 are reset, depending on the value of the Breath_Index and the system goes back to the Sampling Routine until the next event is reached.

Active Mode No Breath Detected Routine
Shift Breath_Registers
Index=Index+1
Breath_Register[1]=TWO_BREATH_TIME
Average_Breath_Rate=[SUM (Breath_Register [2 . . . 5])]/4
If Average_Breath_Rate>SLEEP_BREATH_TIME (10 sec) GOTO SLEEP MODE
If index is odd; Timer_1=TWO_BREATH_TIME;
If index is even; Timer_2=TWO_BREATH_TIME;

If the system is in active mode, and no breath is detected, as indicated by one of the two timers timing out, the Breath_Registers are shifted and a "false breath" is added to Breath_Register[1]. The false breath added to the register is the constant TWO_BREATH_TIME which is selected from between 10 sec to 30 sec. with 15 sec. being typical. After the breaths are shifted, a new Average_Breath_Rate is determined. The new Average_Breath_Rate is then compared to the constant, SLEEP_BREATH_TIME. If Average_Breath_Rate (stored as an average time elapsed per breath) is greater than SLEEP_BREATH_TIME, the system will go into Sleep Mode by lowering the inspiration breath pressure threshold for the pressure sensor. Timer_1 or Timer_2 are reset, depending on the value of the Breath_Index and the system goes back to the Sampling Routine until the next event is reached.

If the system is in Sleep Mode, the Sleep Mode routines are accessed. If a breath is detected while in Sleep Mode, the Sleep Mode Breath Detection Routine is accessed.

Sleep Mode Breath Detection Routine
Shift Breath-Registers
Index=Index+1
If Index is odd; Breath_Register[1]=(MAX_BREATH_TIME−Timer_2)
If Index is even; Breath_Register[1]=(MAX_BREATH_TIME−Timer_1)
Average_Breath_Rate=[SUM (Breath_Register [2 . . . 5])]/4
If Average_Breath_Rate>SLEEP_BREATH_TIME (10 sec) GOTO ACTIVE MODE
If index is odd; Timer_1=TWO_BREATH_TIME;
If index is even; Timer_2=TWO_BREATH_TIME;

When a breath is detected in sleep mode, the routine is similar to the routine above for the active mode. The primary difference is that the Sleep Mode routine looks to see if the device needs to move back to active mode. Specifically, the Average_Breath_Rate is compared to the SLEEP_BREATH_TIME. If the Average_Breath_Rate is greater than the SLEEP_BREATH_TIME, the device will be set to Active Mode, otherwise the device remains in Sleep Mode.

Sleep Mode No Breath Detection Routine
Shift Breath-Registers
Index=Index+1
Breath_Register[1]=TWO_BREATH_TIME
Average_Breath_Rate=[SUM (Breath_Register [2 . . . 5])]/4
If Timer_1+Timer_2>K_FACTOR*Average_Breath_Rate GOTO Automatic $O_2$ Delivery
If index is odd; Timer_1=TWO_BREATH_TIME;
If index is even; Timer_2=TWO_BREATH_TIME;

When no breath is detected before the timers time out, in sleep mode, the results are similar to when the timers time out in active mode. The primary difference is that the Sleep Mode routine looks to see if the device needs to initiate automatic delivery of oxygen enriched gas. Specifically, the elapsed time from Timer_1 and Timer_2 are added and compared to the Average_Breath_Rate*K_FACTOR. K_FACTOR is a constant usually selected from 1.5 to 2.5, with 2.0 being preferred. If the sum of Timer_1 and Timer_2 is greater than the Average_Breath_Rate*K_FACTOR, the device will begin to automatically deliver oxygen enriched gas to the user, in the manner described earlier. The Automatic $O_2$ Delivery Mode routine is set forth below:

Automatic $O_2$ Delivery Mode
Deliver $O_2$ enriched gas every 3-4 sec. varying randomly or according to a predetermined pattern
After each $O_2$ enriched gas deliver:
If Timer_1+Timer_2>K_FACTOR*Average_Breath_Rate
    Yes—Stay in Auto-Dose mode
    No—Go back to Sleep mode; resume Sampling Automatic $O_2$ Delivery Mode is used to provide $O_2$ enriched gas at random or a varying predetermined intervals. After each delivery of $O_2$ enriched gas, the device monitors for the detection of a breath (signaled by a change in the time of either of Timer_1 or Timer_2) while waiting to deliver the next bolus of oxygen enriched gas.

In this manner, the changing of the operating parameters and the automatic delivery of oxygen enriched gas is controlled by the average breath rate, determined by ignoring the time between the penultimate and last breath. This method also avoids having to measure the time since the last breath to initiate changes in the system.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S.

patents, U.S. patent applications, and other materials is specifically not incorporated by reference in this patent.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for controlling release of oxygen enriched gas to a user of an oxygen concentrator that has a sleep mode and an active mode, comprising:
    measuring the time between a plurality of successive breaths, wherein a breath is determined to begin when a drop in pressure is measured using a pressure sensor coupled to an outlet of a conduit coupling the user to an oxygen enriched gas source;
    determining an average time between each of the successive breaths, wherein the time between the penultimate breath and the last breath is not used to determine the average time;
    setting an inspiration breath pressure threshold for the pressure sensed by the pressure sensor based on the determined average time, including:
        setting the inspiration breath pressure threshold to an active mode breath pressure threshold in response to a determination that the average time is less than a predefined time, and
        setting the inspiration breath pressure threshold to a sleep mode breath pressure threshold in response to a determination that the average time is greater than the predefined time, wherein the sleep mode breath pressure threshold is lower than the active mode breath pressure threshold;
    measuring the time since the penultimate breath and the time since the last breath in the sleep mode and determining a sum of the time since the penultimate breath plus the time since the last breath; and
    automatically controlling release of oxygen enriched gas to the user in response to an evaluation that determines whether the sum is greater than a function of the determined average time.

2. The method of claim 1, wherein the predefined time is between about 8 seconds and about 12 seconds.

3. The method of claim 1, wherein the function of the determined average time is a constant times the determined average time, wherein the constant is between 1.5 and 2.5.

4. The method of claim 1, further comprising measuring the time since the penultimate breath, wherein if two breaths are not received within a predetermined time, a false breath time is added to the successive breaths from which the average time between each of the successive breaths is determined.

5. The method of claim 1, wherein the method comprises measuring the time between at least six successive breaths, wherein the time between the 5th breath and the 6th breath is not used to determine the average time.

6. The method of claim 1, wherein adjusting the inspiration breath pressure threshold based on the average time is performed automatically.

7. The method of claim 1, wherein the automatically controlled release of oxygen enriched gas controls release to the user every 3-4 seconds.

8. The method of claim 7, wherein the time between each automatically controlled release of oxygen enriched gas is varied randomly between 3-4 seconds.

9. The method of claim 7, wherein the time between each automatically controlled release of oxygen enriched gas is varied by a constant amount, cycling between 3-4 seconds.

10. The method of claim 1, wherein the automatically controlled release of oxygen enriched gas to the user is discontinued if a breath is detected from the user.

11. The method of claim 1, wherein the oxygen enriched gas source is an oxygen concentrator system.

12. The method of claim 1, wherein the oxygen enriched gas source is an oxygen tank.

13. An oxygen concentrator apparatus, comprising:
    a pressure sensor, the pressure sensor configured to detect a breath pressure of a user; and
    a processor coupled to the pressure sensor and configured to execute non-transitory program instructions, and wherein the program instructions configure the processor to execute the method for controlling release of oxygen enriched gas according to claim 1.

14. The oxygen concentrator apparatus of claim 13, further comprising an oxygen sensor coupled to the processor, wherein the oxygen sensor is capable of detecting oxygen in a gas during use.

15. The oxygen concentrator apparatus of claim 13, wherein the oxygen concentrator weighs less than 5 lbs.

16. The oxygen concentrator apparatus of claim 13, further comprising:
    at least two canisters; and
    gas separation adsorbent disposed in the at least two canisters, wherein the gas separation adsorbent separates at least some nitrogen from air in the canister to produce oxygen enriched gas.

17. A method for controlling release of oxygen enriched gas to a user of an oxygen concentrator, comprising:
    measuring the time between a plurality of successive breaths;
    measuring the time since a penultimate breath was taken and the time since a last breath, wherein a breath is determined to begin when a drop in pressure is measured using a pressure sensor coupled to an outlet of a conduit coupling the user to an oxygen enriched gas source;
    determining an average time between each of the successive breaths, wherein the time between the penultimate breath and the last breath is not used to determine the average time;
    determining a sum of the time since the penultimate breath plus the time since the last breath; and
    automatically controlling release of oxygen enriched gas to the user in response to an evaluation that determines whether the sum is greater than a function of the determined average time.

18. The method of claim 17, wherein the automatically controlling release of oxygen enriched gas controls release of oxygen enriched gas to the user every 3-4 seconds.

19. The method of claim 17, wherein the time between each automatically controlled release of oxygen enriched gas is varied randomly between 3-4 seconds.

20. The method of claim 17, wherein the time between each automatic controlled release of oxygen enriched gas is varied by a constant amount, cycling between 3-4 seconds.

21. The method of claim 17, wherein the automatically controlled release of oxygen enriched gas to the user is discontinued if a breath is detected from the user.

22. The method of claim 17, wherein the oxygen enriched gas source is an oxygen concentrator system.

23. The method of claim 17, wherein the oxygen enriched gas source is an oxygen tank.

24. An oxygen concentrator apparatus, comprising:
a pressure sensor configured to detect a breath pressure of a user, the pressure sensor coupled to an outlet of a conduit for coupling the user to an oxygen enriched gas source; and
a processor coupled to the pressure sensor and configured to:
measure the time between a plurality of successive breaths;
measure the time since a penultimate breath was taken and the time since a last breath, wherein a breath is determined to begin when a drop in pressure is measured using the pressure sensor;
determine an average time between each of the successive breaths, wherein the time between the penultimate breath and the last breath is not used to determine the average time;
determine a sum of the time since the penultimate breath plus the time since the last breath; and
automatically control release of oxygen enriched gas to the user in response to an evaluation that determines whether the sum is greater than a function of the determined average time.

25. The oxygen concentrator apparatus of claim 24, wherein the automatically controlled release of oxygen enriched gas controls release of oxygen enriched gas to the user every 3-4 seconds.

26. The oxygen concentrator apparatus of claim 24, wherein the time between each automatically controlled release of oxygen enriched gas is varied randomly between 3-4 seconds.

27. The oxygen concentrator apparatus of claim 24, wherein the time between each automatically controlled release of oxygen enriched gas is varied by a constant amount, cycling between 3-4 seconds.

28. The oxygen concentrator apparatus of claim 24, wherein the automatically controlled release of oxygen enriched gas to the user is discontinued if a breath is detected from the user.

* * * * *